US010206598B2

(12) United States Patent
Bounyong et al.

(10) Patent No.: US 10,206,598 B2
(45) Date of Patent: Feb. 19, 2019

(54) MUSCULAR FATIGUE DETERMINATION APPARATUS, METHOD FOR DETERMINING MUSCULAR FATIGUE, AND RECORDING MEDIUM

(71) Applicant: Panasonic Intellectual Property Management Co., Ltd., Osaka (JP)

(72) Inventors: Souksakhone Bounyong, Osaka (JP); Koji Morikawa, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 630 days.

(21) Appl. No.: 14/946,727

(22) Filed: Nov. 19, 2015

(65) Prior Publication Data
US 2016/0157743 A1 Jun. 9, 2016

(30) Foreign Application Priority Data

Dec. 3, 2014 (JP) .................................. 2014-245223

(51) Int. Cl.
*A61B 5/04* (2006.01)
*A61B 5/11* (2006.01)
*A61B 5/00* (2006.01)
*A61B 5/0488* (2006.01)

(52) U.S. Cl.
CPC ........ *A61B 5/04012* (2013.01); *A61B 5/0488* (2013.01); *A61B 5/11* (2013.01); *A61B 5/6804* (2013.01); *A61B 5/6895* (2013.01); *A61B 2562/0219* (2013.01); *A61B 2562/0252* (2013.01)

(58) Field of Classification Search
CPC combination set(s) only.
See application file for complete search history.

(56) References Cited

U.S. PATENT DOCUMENTS

2007/0232869 A1* 10/2007 Kanzaki ............. A61B 5/04012
600/300
2007/0276282 A1 11/2007 Fukumura et al.
2013/0184539 A1* 7/2013 Buchenrieder .... A61B 5/04012
600/301

FOREIGN PATENT DOCUMENTS

CN 101244753 A * 8/2008
CN 101244753 B * 7/2010
(Continued)

*Primary Examiner* — Scott T Luan
(74) *Attorney, Agent, or Firm* — Wenderoth, Lind & Ponack, L.L.P.

(57) ABSTRACT

A muscular fatigue determination apparatus includes an information obtaining unit that obtains loads applied to a pedal of a bicycle, rotation speeds of a crank of the bicycle, and myoelectric potentials of a user, the myoelectric potentials and the loads being in a one-to-one relationship, the myoelectric potentials and the rotation speeds being in a one-to-one relationship, and a muscular fatigue information generation unit that generates muscular fatigue information regarding the user on the basis of whether a difference between the myoelectric potentials of the user is larger than a first threshold, each of the myoelectric potentials being associated to a load range that is one of load ranges and to a rotation speed range that is one of rotation speed ranges, each of the loads belonging to one of the load ranges and each of the rotation speed ranges belonging to one of the rotation speed ranges.

10 Claims, 15 Drawing Sheets

(56) References Cited

FOREIGN PATENT DOCUMENTS

| JP | 2000-000232 | 1/2000 |
|----|-------------|--------|
| JP | 2007-312921 | 12/2007 |

* cited by examiner

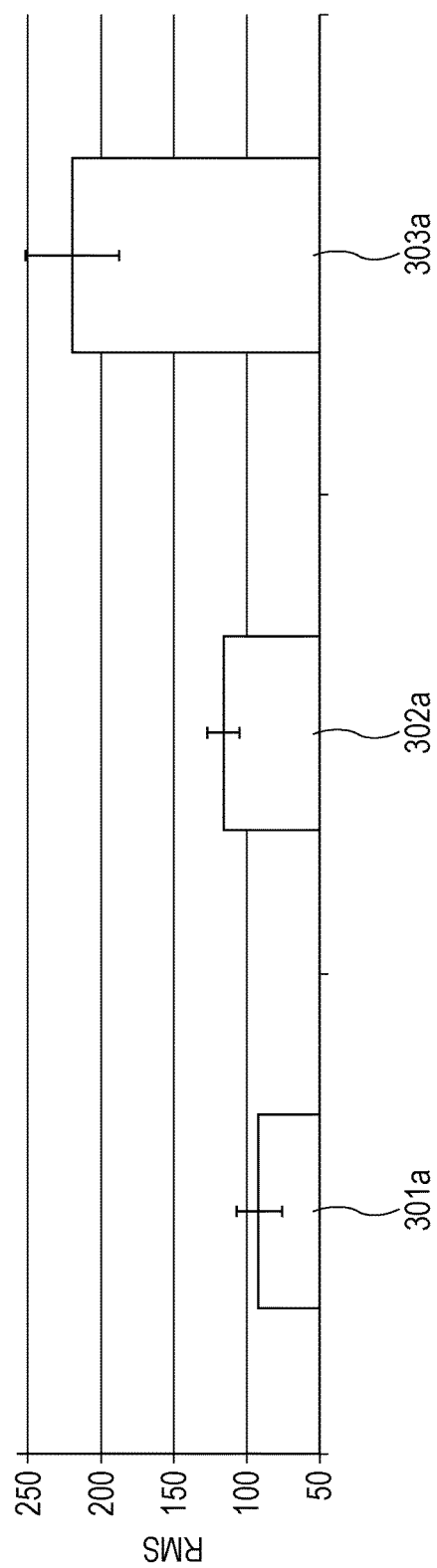

FIG. 4A

| LOAD GROUP | TEMPORAL RMSs OF MYOELECTRIC POTENTIALS (OBTAINED EVERY 30 SECONDS) | | | | | | | |
|---|---|---|---|---|---|---|---|---|
| 1 | 80 | 90 | | | | | | |
| 2 | | 90 | 115 | 110 | 102 | | | |
| 3 | | | | | 120 | | 184 | 162 | 135 | 169 |
| 4 | | | | | | 150 | 196 | 220 | |
| MUSCULAR FATIGUE DETERMINATION | N | N | N | N | N | N | Y | Y | Y | Y |

MUSCULAR FATIGUE OCCURS

Y: MUSCULAR FATIGUE
N: NO MUSCULAR FATIGUE

FIG. 4B

| LOAD GROUP | ROTATION SPEED rpm | TEMPORAL RMSs OF MYOELECTRIC POTENTIALS (OBTAINED EVERY 30 SECONDS) | | | | | | | | | | | |
|---|---|---|---|---|---|---|---|---|---|---|---|---|---|
| 1 | 40→59 | 80 | | | | | | | | | | | |
| 1 | 60→79 | | 90 | | | | | | | | | | |
| 1 | 80→100 | | | | | 120 | | | | | | | |
| 2 | 40→59 | | | 90 | | 96 | | | | | | | |
| 2 | 60→79 | | | | 110 | | | | | | | | |
| 2 | 80→100 | | | | 115 | | | | | | | | |
| 3 | 40→59 | | | | | | | 150 | | | | | |
| 3 | 60→79 | | | | | | | | | 184 | 162 | | |
| 3 | 80→100 | | | | | | | | | | 162 | 135 | |
| 4 | 40→59 | | | | | | | | 196 | | | | |
| 4 | 60→79 | | | | | | | | | 220 | | | |
| 4 | 80→100 | | | | | | | | | | | | 169 |

FIG. 10

| LOAD GROUP | ROTATION SPEED rpm | TEMPORAL RMSs OF MYOELECTRIC POTENTIALS (OBTAINED EVERY 30 SECONDS) | | | | | | | | | | | | | |
|---|---|---|---|---|---|---|---|---|---|---|---|---|---|---|---|
| 1 | 40→59 | 80 | | | | | | | | | | | | | |
| 1 | 60→79 | | 90 | | | | | | | | | | | | |
| 1 | 80→100 | | | 90 | | 120 | | | | | | | | | |
| 2 | 40→59 | | | | 96 | | | | | | | | | | |
| 2 | 60→79 | | | | 110 | | | | | | | | | | |
| 2 | 80→100 | | | 115 | | | | | | | | | | | |
| 3 | 40→59 | | | | | | | | 135 | | | | | | |
| 3 | 60→79 | | | | | | | 162 | 169 | | | | | | |
| 3 | 80→100 | | | | | | 184 | | | | 196 | 222 | | | |
| 4 | 40→59 | | | | | | | | | 150 | 196 | | | | |
| 4 | 60→79 | | | | | | | | | | | | 230 | 175 | |
| 4 | 80→100 | | | | | | | | 220 | | | | | 135 135 | 170 |

FIG. 11A

| ROTATION SPEED [rpm] / LOAD GROUP | 40→59 | 60→79 | 80→100 |
|---|---|---|---|
| 1 | 1.1 | 1 | 0.8 |
| 2 | 1.15 | 1 | 0.85 |
| 3 | 1.2 | 1 | 0.9 |
| 4 | 1.25 | 1 | 0.95 |

FIG. 11B

| LOAD GROUP | TEMPORAL RMSs OF MYOELECTRIC POTENTIALS (OBTAINED EVERY 30 SECONDS) | | | | | | | | | |
|---|---|---|---|---|---|---|---|---|---|---|
| 1 | 80 | 90 | | | 96 | | | | | |
| 2 | | | 104 | 98 | 110 | 110 | | | | |
| 3 | | | | | | | 166 | 162 | 162 | 169 | 204 |
| 4 | | | | | | | 188 | 196 | 209 | | 196 | 200 | 219 | 135 | 135 |
| MUSCULAR FATIGUE DETERMINATION | N | N | N | N | N | N | N | N | N | N | N | N | 230 | Y | Y | Y | Y |

F1 (highlighting 230 / Y)

Y: MUSCULAR FATIGUE
N: NO MUSCULAR FATIGUE

LEVEL OF MUSCULAR FATIGUE = 100% × (230 − 188)/30 = 140%
OR
LEVEL OF MUSCULAR FATIGUE = (230 − 188) − 30 = 12

MUSCULAR FATIGUE DETERMINATION APPARATUS, METHOD FOR DETERMINING MUSCULAR FATIGUE, AND RECORDING MEDIUM

BACKGROUND

1. Technical Field

The present disclosure relates to a muscular fatigue determination apparatus, a method for determining muscular fatigue, and a recording medium that generate muscular fatigue information regarding a user and that determine presence or absence of muscular fatigue or a level of muscular fatigue on the basis of a relationship between a load applied to a pedal, the rotation speed of a crank, and the myoelectric potential of the user while the user is rotating the crank by stepping on the pedal of a bicycle or a cycle trainer.

2. Description of the Related Art

There have been a lot of studies on myoelectric potential. Due to characteristics of myoelectric potential, the amplitude of myoelectric potential increases as muscular output increases, and the amplitude of myoelectric potential decreases as muscular output decreases. If muscular fatigue occurs, more exercise units (muscle fibers) than before the occurrence of the muscular fatigue are needed to generate the same force (in the case of an isometric exercise), and the amplitude of myoelectric potential increases. In the case of an isometric exercise, an average frequency of myoelectric potential decreases as muscle fatigues.

Some methods for evaluating a state of muscle during exercise or the like on the basis of the characteristics of myoelectric potential have been proposed. In Japanese Unexamined Patent Application Publication No. 2000-000232, for example, a method for determining muscular fatigue during driving has been proposed. An electrical stimulation electrode pulse voltage is applied to a muscle of a driver, an evoked myoelectric potential caused by the application of the pulse voltage is measured, a power spectrum of the evoked myoelectric potential is obtained, and a center frequency of the power spectrum is calculated and stored as an initial value. The same operation is performed at certain time intervals, and it is determined whether muscular fatigue has occurred on the basis of changes in the center frequency of the power spectrum.

In Japanese Unexamined Patent Application Publication No. 2007-312921, a method for determining whether a user has appropriately recovered from exercise has been proposed. Before beginning the exercise, the user performs an isometric exercise to measure a myoelectric potential. After the exercise, the user performs an isometric exercise to measure a myoelectric potential again with the same load as in the isometric exercise performed before the exercise. It is then determined whether the user has appropriately recovered from the exercise by comparing the second myoelectric potential with the first myoelectric potential.

SUMMARY

The method disclosed in Japanese Unexamined Patent Application Publication No. 2000-000232, however, might be dangerous since electric stimulation is applied to the user and resultant information is used as an initial value. In Japanese Unexamined Patent Application Publication No. 2007-312921, a preliminary isometric exercise needs to be performed before a main exercise to measure a myoelectric potential, which is troublesome. As another method, a method for measuring blood lactic acid concentration during exercise, for example, is known especially in a sport field, but it is difficult for general users to use this method.

In an actual exercise, a user might want to know a muscular fatigue state thereof in real-time during the exercise. When the user is pedaling a bicycle, for example, a load applied to a pedal constantly varies, and it is difficult to maintain the same load as in Japanese Unexamined Patent Application Publication No. 2007-312921.

One non-limiting and exemplary embodiment provides a muscular fatigue determination apparatus capable of generating muscular fatigue information in real-time while a user is pedaling a bicycle.

In one general aspect, the techniques disclosed here feature a muscular fatigue determination apparatus including a load detector that detects loads applied to a pedal of a bicycle, a rotation speed detector that detects rotation speeds of a crank of the bicycle, a myoelectric potential detector that detects myoelectric potentials of a user, an information obtainer that obtains the loads, the rotation speeds, and the myoelectric potentials, the myoelectric potentials and the loads being in a one-to-one relationship, the myoelectric potentials and the rotation speeds being in a one-to-one relationship, and a muscular fatigue information generator that generates muscular fatigue information regarding the user on the basis of whether a difference between the myoelectric potentials of the user is larger than a first threshold, each of the myoelectric potentials being associated to a load range that is one of load ranges and to a rotation speed range that is one of rotation speed ranges, each of the loads belonging to one of the load ranges and each of the rotation speed ranges belonging to one of the rotation speed ranges.

According to the present disclosure, muscular fatigue information regarding a user can be generated, without performing calibration in advance, on the basis of a relationship between a load applied to a pedal, the rotation speed of a crank, and the myoelectric potential of the user while the user is rotating the crank by stepping on the pedal of a bicycle or a cycle trainer, and presence or absence of muscular fatigue or a level of muscular fatigue can be determined in real-time.

The load applied to the pedal refers to force applied to the pedal or torque applied to a crank axle on the basis of the force applied to the pedal.

It should be noted that general or specific embodiments may be implemented as a system, a method, an integrated circuit, a computer program, a computer-readable recording medium, or any selective combination thereof. The computer-readable recording medium may be a nonvolatile recording medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3D is a diagram illustrating root mean squares (RMSs) obtained with the certain load and the three different rotation speeds;

FIG. 4A is a diagram illustrating measured myoelectric potentials classified in accordance with loads;

FIG. 4B is a diagram illustrating measured myoelectric potentials classified in accordance with loads and rotation speed;

FIG. 10 is a diagram illustrating an example of a database created by a database creation portion storing data classified in accordance with torque and rotation speed (the number of rotations) before feature values of myoelectric potentials are corrected;

FIG. 11A is a diagram illustrating correction coefficients for myoelectric potentials based on load groups and rotation speed;

FIG. 11B is a diagram illustrating data stored after the myoelectric potentials are corrected on the basis of the rotation speed of a crank;

DETAILED DESCRIPTION

Before an embodiment of the present disclosure is described in detail with reference to the drawings, experiments conducted by the present inventors and knowledge obtained from the experiments, which forms the basis of the present disclosure, will be described hereinafter.

Experiments and Underlying Knowledge Forming Basis of the Present Disclosure

The experiments conducted by the present inventors will be described.

Figure 1A:
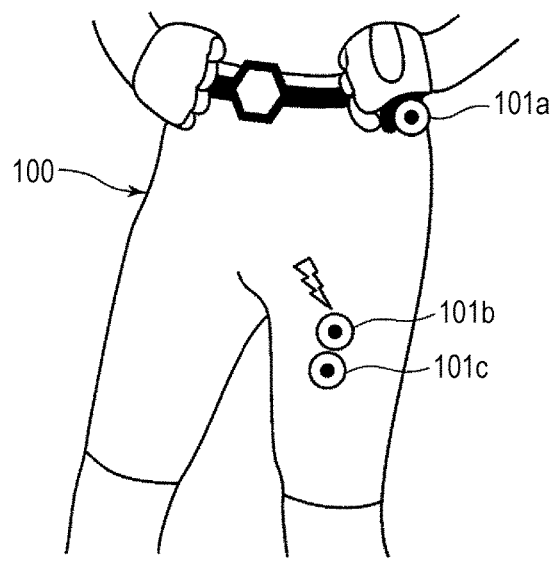
FIG. 1A is a diagram illustrating pedaling experiments.
Figure 1B:
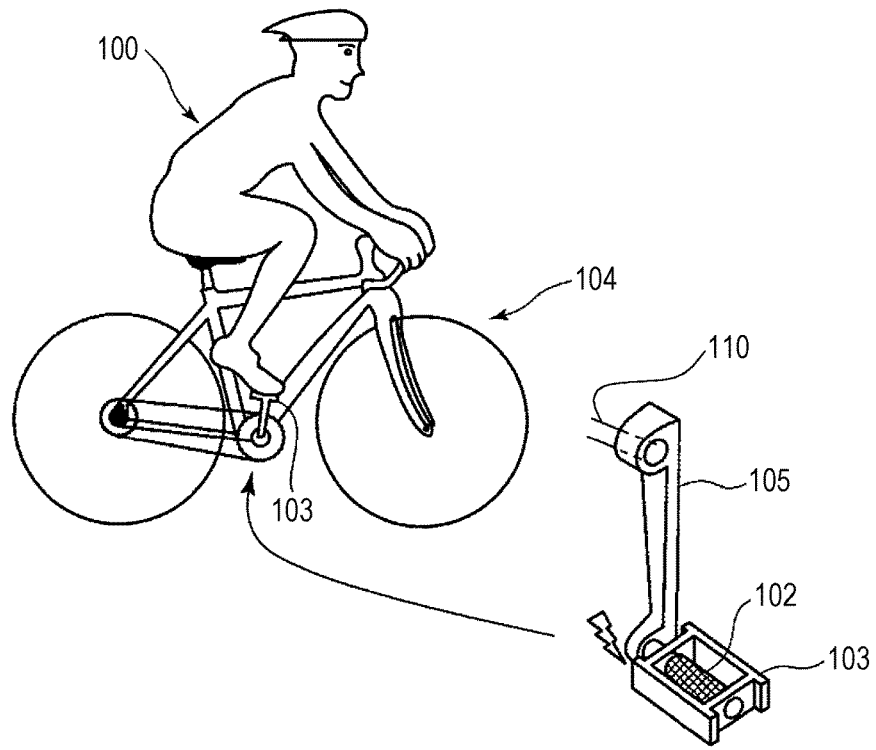
FIG. 1B is a diagram illustrating the pedaling experiments.

FIGS. 1A and 1B illustrate devices used in the experiments. Two electrodes 101b and 101c were attached to the center of a rectus femoris muscle of a subject 100. A distance between the centers of the electrodes 101b and 101c was 2 cm, and a potential difference (electrode 101b—electrode 101c) between the two electrodes 101b and 101c was obtained as the myoelectric potential of the rectus femoris muscle. A ground electrode 101a was attached to a pelvis of the subject 100, and the subject 100 pedaled a cycle trainer.

A load sensor (torque was regarded as the load in these experiments) and a rotation speed sensor 102 were mounted on a pedal 103 of the cycle trainer. The load sensor may be a torque sensor that measures torque applied by the user (subject) of the cycle trainer to a crank axle 110 of the cycle trainer (in the following description, torque that the user applies to the crank axle 110 and torque applied to the crank axle 110 will also be referred to simply as "torque"). Alternatively, the load sensor may be a force sensor that detects force that the user of the cycle trainer applies to the pedal 103. The torque or force measured by the load sensor, the rotation speed of a crank 105 measured by the rotation speed sensor 102, and a myoelectric potential corresponding to the torque or force and the rotation speed were stored in a storage unit, which is not illustrated. The torque applied to the cycle trainer may be calculated on the basis of a value detected by the force sensor and the length of the crank 105 (e.g., a distance between the crank axle 110 and the pedal 103). Since the length of the crank 105 remains the same, the torque applied to the cycle trainer may be a value detected by the force sensor, instead.

Two experiments (a first experiment and a second experiment) were conducted. In the first experiment, the subject 100 pedaled the cycle trainer while maintaining a rotation speed of the crank 105 of 60 rpm (60 rotations per minute) with varying loads. In the second experiment, the subject 100 pedaled the cycle trainer while changing the rotation speed of the crank 105 with a constant load.

Figure 2:
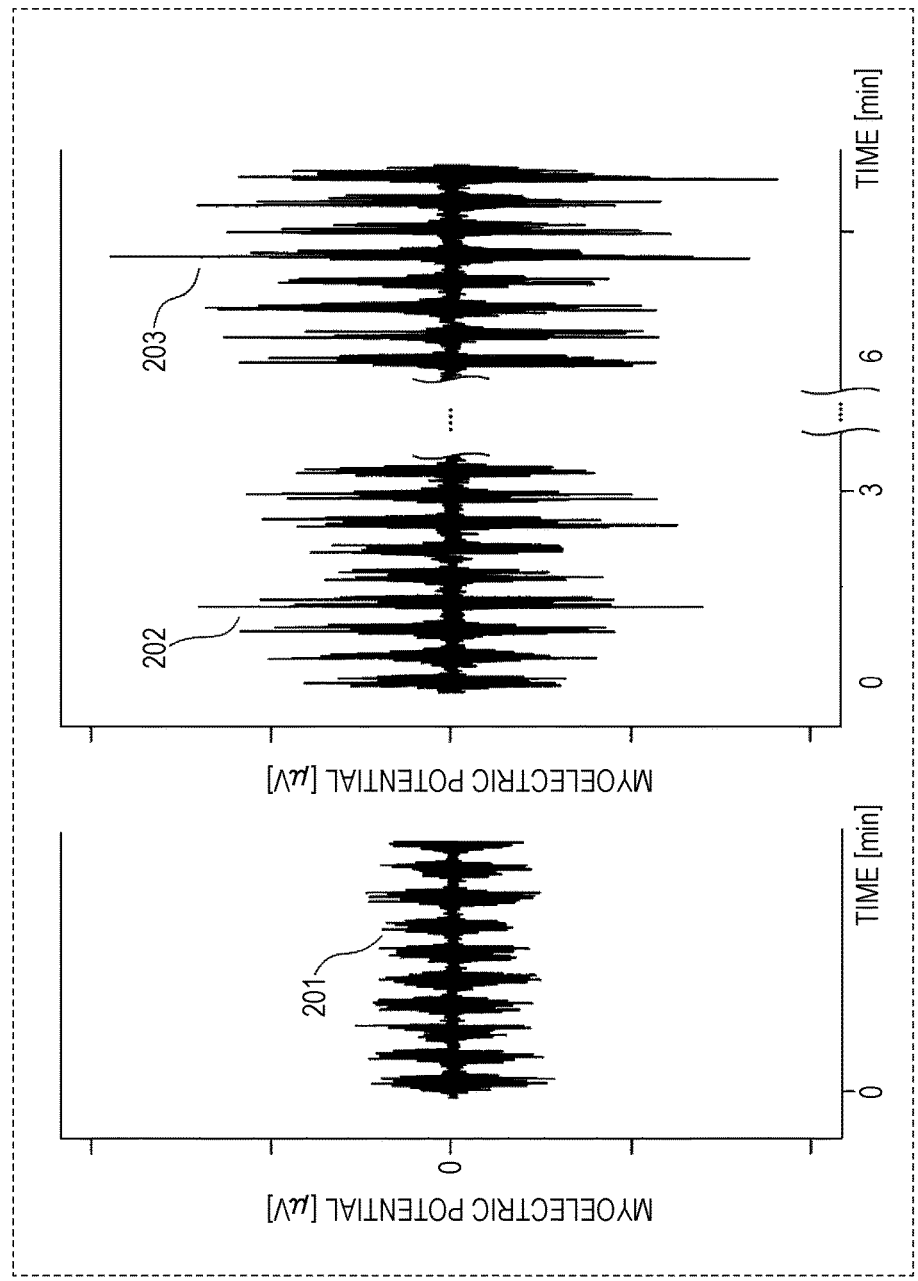
FIG. 2 is a diagram illustrating electromyograms obtained as a result of pedaling of a bicycle.

FIG. 2 illustrates electromyograms obtained as a result of the first experiment. The electromyograms illustrated in FIG. 2 were obtained by measuring the myoelectric potential of the rectus femoris muscle during pedaling using an electromyograph. The vertical axis represents myoelectric potential [$\mu V$], and the horizontal axis represents time [min]. A waveform 201 was obtained by pedaling the cycle trainer with a power of 100 watt. Waveforms 202 and 203 were obtained by pedaling the cycle trainer with a power of 175 watt. The power is a value obtained by multiplying the rotation speed and the torque.

Since an exercise load used for obtaining the waveform 202 was larger than an exercise load used for obtaining the waveform 201, the amplitude of the waveform 202 was larger than that of the waveform 201 as illustrated in FIG. 2.

Although the waveforms 202 and 203 were obtained by pedaling the cycle trainer with the same power, the amplitude of the waveform 203 was larger than that of the waveform 202. The reason why the amplitude of myoelectric potential increased was that the muscle fatigued when a certain period of time has elapsed since a beginning of the pedaling with a power of 175 watt. The mechanism of muscular fatigue has still not been elucidated, but a principal cause is considered to be an increase in the number of exercise units (muscle fibers) of muscle that participate in pedaling, an increase in the frequency of impulses in muscle, or synchronization of firing activities between exercise units.

The second experiment, however, suggested that it was difficult to estimate muscular fatigue only on the basis of the exercise load.

Figure 3A:
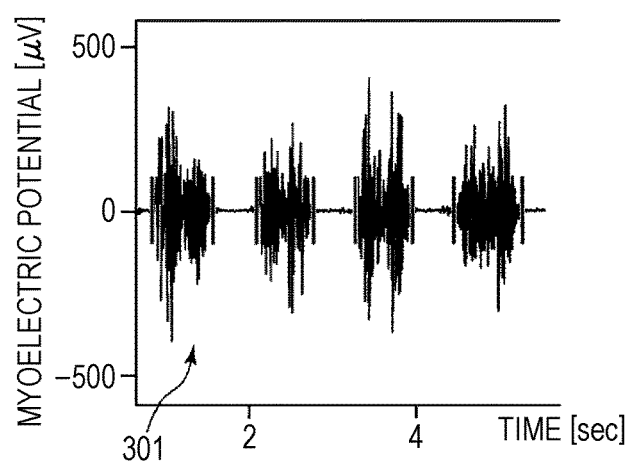
FIG. 3A is a diagram illustrating an electromyogram obtained with a certain load and a rotation speed of 50 rpm.
Figure 3B:
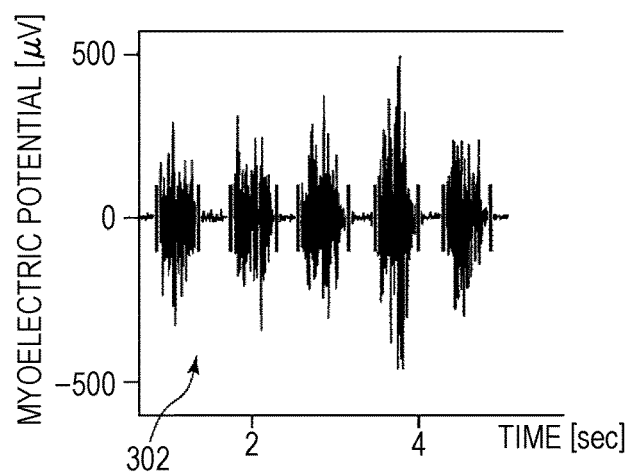
FIG. 3B is a diagram illustrating an electromyogram obtained with the certain load and a rotation speed of 70 rpm.

FIGS. 3A to 3D illustrates results of the second experiment. A waveform 301 illustrated in FIG. 3A represents myoelectric potentials obtained by pedaling the cycle trainer a plurality of rotations in a certain period at a rotation speed of 50 rpm (FIG. 3A illustrates part of the pedaling, that is, four rotations). A waveform 302 illustrated in FIG. 3B represents myoelectric potentials obtained by pedaling the cycle trainer a plurality of rotations in a certain period at a rotation speed of 70 rpm (FIG. 3B illustrates part of the pedaling, that is, five rotations). A waveform 303 illustrated in FIG. 3O represents myoelectric potentials obtained by pedaling the cycle trainer a plurality of rotations in a certain period at a rotation speed of 90 rpm (FIG. 30 illustrates part of the pedaling). Data 301a illustrated in FIG. 3D indicates variation in a plurality of RMSs relating to the pedaling in a plurality of periods at a rotation speed of 50 rpm and an average of the plurality of RMSs. The pedaling in each of the plurality of periods at a rotation speed of 50 rpm and each of the plurality of RMSs are in one-to-one correspondence. Data 302a illustrated in FIG. 3D indicates variation in a plurality of RMSs relating to the pedaling in a plurality of periods at a rotation speed of 70 rpm and an average of the plurality of RMSs. The pedaling in each of the plurality of periods at a rotation speed of 70 rpm and each of the plurality of RMSs are in one-to-one correspondence. Data 303a illustrated in FIG. 3D indicates variation in a plurality of RMSs relating to the pedaling in a plurality of periods at a rotation speed of 90 rpm and an average of the plurality of RMSs. The pedaling in each of the plurality of periods at a rotation speed of 90 rpm and each of the plurality of RMSs are in one-to-one correspondence.

As illustrated in FIG. 3D, the average of the plurality of RMSs relating to the waveform 301, the average of the plurality of RMSs relating to the waveform 302, and the average of the plurality of RMSs relating to the waveform 303 become larger in this order. Since an RMS of myoelectric potentials becomes larger as the rotation speed increases, it can be assumed that an accuracy of estimating muscular fatigue can be improved by taking into consideration the rotation speed as well as the exercise load and the myoelectric potential.

Figure 3C:
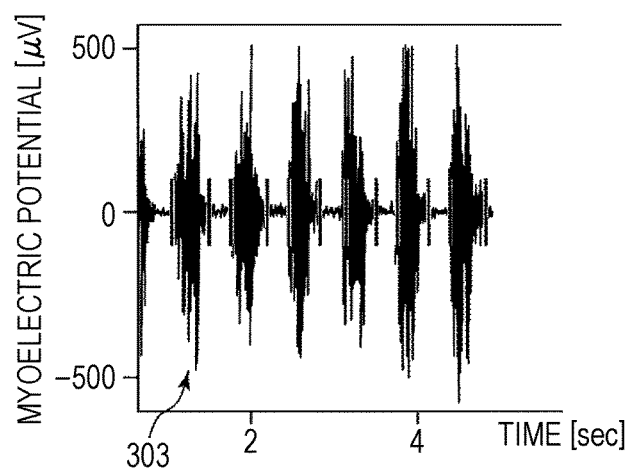
FIG. 3C is a diagram illustrating an electromyogram obtained with the certain load and a rotation speed of 90 rpm.

As a feature value of myoelectric potential as an example of load information used in an embodiment of the present disclosure, any of an RMS of myoelectric potentials in a certain period illustrated in FIG. 3D, an average rectified value (ARV) of an absolute value of amplitude, and an integrated electromyogram (IEMG) may be used. If an RMS is used as a feature value of myoelectric potential, periods in which force is applied are detected and an RMS in each period is calculated as illustrated in FIGS. 3A to 3C, and then an average of the RMSs in all the periods is calculated to obtain the feature value of myoelectric potential.

FIGS. 4A and 4B illustrate recorded myoelectric potentials. In FIG. 4A, a load during pedaling, that is, torque, and a corresponding myoelectric potential were measured every 0.001 second without taking into consideration rotation speed. An RMS of myoelectric potentials was obtained every 30 seconds and stored in the storage unit while classifying the corresponding load into one of four load groups. Muscular fatigue was determined using the stored data. In this example, if a difference between a current RMS of myoelectric potentials (during the measurement of the myoelectric potentials) and a first RMS of myoelectric potentials obtained for the same load group became equal to or larger than a muscular fatigue threshold, namely 30, a muscular fatigue determination unit 406b determined that muscular fatigue had occurred. The muscular fatigue threshold may be obtained from an experiment in which a relationship between myoelectric potential and blood lactic add concentration is investigated. The muscular fatigue threshold may be set on the basis of an experiment in which changes in the relationship between myoelectric potential and blood lactic add concentration are investigated, instead. In a more specific example, if a difference between a first value and a latest value became equal to or larger than the muscular fatigue threshold, namely 30, the muscular fatigue determination unit 406b determined that muscular fatigue had occurred. In a field of the fatigue determination, "N" indicates that muscular fatigue has not occurred, and "Y" indicates that muscular fatigue has occurred. The muscular fatigue threshold can be different between genders or age groups. The muscular fatigue threshold may be set for each gender or age group through experiments.

Since a current RMS of myoelectric potentials increased to 196 from 150, which is a first RMS of myoelectric potentials, for load group 4, the difference became 46. The muscular fatigue determination unit 406b therefore determined that muscular fatigue had occurred.

It may be determined whether muscular fatigue has occurred in consideration of the load and the rotation speed during pedaling. FIG. 4B illustrates a case in which myoelectric potentials were classified into one of a plurality of load groups while taking into consideration the load and the rotation speed during pedaling. In this example, myoelectric potentials were stored while classifying a corresponding load into one of the four load groups and a corresponding rotation speed into one of three rotation speed groups for each load group. The myoelectric potential can increase not because of muscular fatigue but because of the rotation speed. By correcting measured myoelectric potentials while taking into consideration the rotation speed as well as the load, it becomes possible to increase an accuracy of determining muscular fatigue during pedaling.

A muscular fatigue determination apparatus and a method for determining muscular fatigue according to an embodiment of the present disclosure conceived from the results of the above experiments may at least include an information obtaining unit 400 that associates a load applied to the pedal 103 of a bicycle (includes a cycle trainer) 104 pedaled by the user 100, the rotation speed of the crank 105, a myoelectric potential of the user 100 corresponding to the load applied to the pedal 103 and the rotation speed of the crank 105, and a point of time with one another and a muscular fatigue information generation unit 399 that compares myoelectric potentials at different times obtained by the information obtaining unit 400 and associated with loads and rotation speeds, each belonging to any of a plurality of groups for different ranges of values, to generate muscular fatigue information regarding the user 100 on the basis of a result of the comparison. Here, a load and a rotation speed, each belonging to any of the plurality of groups for different ranges of values, are, at least, a load belonging to any of a plurality of load groups for different ranges of values and a rotation speed associated with the load belonging to any of such load groups. Alternatively, a load and a rotation speed, each belonging to any of the plurality of groups for different ranges of values, are a load belonging to any of a plurality of load groups for different ranges of values and a rotation speed associated with the load belonging to any of such load groups and classified into one of a plurality of rotation speed groups for difference ranges of values.

A myoelectric potential associated with a load and a rotation speed, each belonging to any of the plurality of groups for different ranges of values, may be an RMS of myoelectric potential classified into one of a plurality of groups in accordance with the load (torque) and the rotation speed. How to classify each RMS of a plurality of myoelectric potentials into one of the load groups (torque groups) may be determined on the basis of an average of a plurality of loads measured by the load sensor (torque sensor) corresponding to the plurality of myoelectric potentials measured in a certain period (e.g., 30 seconds) in which each RMS of the plurality of myoelectric potentials has been calculated. How to classify each RMS of a plurality of myoelectric potentials into one of the rotation speed groups may be determined on the basis of an average of a plurality of rotation speeds measured by the rotation speed sensor corresponding to the plurality of myoelectric potentials measured in the certain period (e.g., 30 seconds) in which each RMS of the plurality of myoelectric potentials has been calculated. In the example illustrated in FIG. 4B, the number of load groups is 4, and the number of rotation speed groups in each group, that is, for example, in load group 1, is 4. If a correlation between muscular fatigue and myoelectric potential can be found, an average of a plurality of myoelectric potentials may be used instead of an RMS of myoelectric potentials.

The muscular fatigue information generation unit 399 can therefore compare RMSs of myoelectric potentials at different times associated with rotation speeds associated with loads, each belonging to one of the plurality of load groups for different ranges of values, or rotation speeds, each belonging to one of the plurality of rotation speed groups for different ranges of values (RMSs of myoelectric potentials whose load groups and rotation speed groups are the same, that is, in FIG. 4B, for example, an RMS of myoelectric potentials of 90 associated with a rotation speed of 40 to 59 rpm in load group 2 and an RMS of myoelectric potentials of 96 associated with a rotation speed of 40 to 59 rpm in load group 2), with each other and generate muscular fatigue information regarding the user 100 on the basis of a result of the comparison.

Embodiment

An embodiment of the present disclosure will be described in detail hereinafter with reference to the drawings.

Before describing an embodiment of the present embodiment in detail with reference to the drawings, various aspects of the present disclosure will be described.

According to a first aspect of the present disclosure, a muscular fatigue determination apparatus is provided including a load detector that detects loads applied to a pedal of a bicycle, a rotation speed detector that detects rotation speeds of a crank of the bicycle, a myoelectric potential detector that detects myoelectric potentials of a user, an information obtainer that obtains the loads, the rotation speeds, and the myoelectric potentials, the myoelectric potentials and the loads being in a one-to-one relationship, the myoelectric potentials and the rotation speeds being in a one-to-one relationship, and a muscular fatigue information generator that generates muscular fatigue information regarding the user on the basis of whether a difference between the myoelectric potentials of the user is larger than a first threshold, each of the myoelectric potentials being associated to a load range that is one of load ranges and to a rotation speed range that is one of rotation speed ranges, each of the loads belonging to one of the load ranges and each of the rotation speed ranges belonging to one of the rotation speed ranges.

According to this aspect, muscular fatigue information regarding the user can be generated, without performing calibration in advance, on the basis of a relationship between the load applied to the pedal, the rotation speed of the crank, and the myoelectric potential of the user while the user is rotating the crank by stepping on the pedal of a bicycle or a cycle trainer, and presence or absence of muscular fatigue or a level of muscular fatigue can be determined in real-time.

According to a second aspect of the present disclosure, the muscular fatigue determination apparatus according to the first aspect is provided in which, if the difference between the myoelectric potentials of the user is larger than the first threshold, the muscular fatigue information generator generates muscular fatigue information regarding the user indicating that muscular fatigue has occurred.

According to this aspect, muscular fatigue information regarding the user can be generated, without performing calibration in advance, on the basis of the relationship between the load applied to the pedal, the rotation speed of the crank, and the myoelectric potential of the user while the user is rotating the crank by stepping on the pedal of the bicycle or the cycle trainer, and presence or absence of muscular fatigue or the level of muscular fatigue can be determined in real-time.

According to a third aspect of the present disclosure, the muscular fatigue determination apparatus according to the first aspect is provided in which the information obtainer obtains the loads, the rotation speeds, and the myoelectric potentials of the user while associating the loads, the rotation speeds, and the myoelectric potentials of the user with a point of time. The muscular fatigue information generator generates the muscular fatigue information regarding the user on the basis of whether a difference between the myoelectric potentials of the user each corresponding to the load range that is one of the load ranges and to the rotation speed range that is one of the rotation speed ranges, and each associated with different points of time is larger than the first threshold.

According to this aspect, muscular fatigue information regarding the user can be generated, without performing calibration in advance, on the basis of the relationship between the load applied to the pedal, the rotation speed of the crank, and the myoelectric potential of the user while the user is rotating the crank by stepping on the pedal of the bicycle or the cycle trainer, and presence or absence of muscular fatigue or the level of muscular fatigue can be determined in real-time.

According to a fourth aspect of the present disclosure, the muscular fatigue determination apparatus according to the first aspect is provided further including an outputter that outputs the muscular fatigue information generated by the muscular fatigue information generator.

According to this aspect, the outputter can output the muscular fatigue information generated by the muscular fatigue information generator to visually feed the muscular fatigue information back to the user. A liquid crystal display device or the like, for example, which is an example of the outputter, can display the rotation speed, the power of the user's left and right legs, a muscular fatigue state, the level of muscular fatigue, or the like to inform the user of such information.

According to a fifth aspect of the present disclosure, the muscular fatigue determination apparatus according to the first aspect is provided in which the information obtainer further includes a load classifier that classifies each the loads obtained by the information obtainer into one of a plurality of load groups on the basis of a value of the load. The muscular fatigue information generator compares the myoelectric potentials in the same load group with each other for each of the plurality of load groups into which loads have been classified by the load classifier and generates the muscular fatigue information regarding the user.

According to this aspect, by comparing the myoelectric potentials in the same load group with each other for each of the plurality of load groups into which the loads have been classified by the load classifier, the adjacent loads can be compared with each other, and an accuracy of determining presence or absence of muscular fatigue or the level of muscular fatigue on the basis of the muscular fatigue information can be increased.

According to a sixth aspect of the present disclosure, the muscular fatigue determination apparatus according to the fifth aspect is provided in which the information obtainer further includes a myoelectric potential corrector that corrects a myoelectric potential corresponding to one of the load groups into which the load has been classified by the load classifier, the myoelectric potentials including the myoelectric potential, the correction being made based on the rotation speed corresponding to the myoelectric potential. When comparing the myoelectric potentials in the same load group with each other for each of the plurality of load groups into which the loads have been classified by the load classifier, the muscular fatigue information generator compares the myoelectric potentials with each other using the myoelectric potential corrected by the myoelectric potential corrector and generates the muscular fatigue information regarding the user.

According to this aspect, the myoelectric potential corrector can correct a difference between myoelectric potentials caused by different rotation speeds, the myoelectric potentials corresponding to loads in the same load group obtained by the load information obtainer. The muscular fatigue information generator can compare the myoelectric potentials corresponding to the loads in the same load group with each other, and the accuracy of determining presence or absence of muscular fatigue or the level of muscular fatigue on the basis of the muscular fatigue information can be increased.

According to a seventh aspect of the present disclosure, the muscular fatigue determination apparatus according to the fifth aspect is provided in which the muscular fatigue information generator includes a myoelectric potential comparer that obtains a difference between a first myoelectric potential and a latest myoelectric potential in the same load group among the plurality of load groups into which the loads have been classified by the load classifier, the myoelectric potentials of the user include the first myoelectric potential and the latest myoelectric potential, and a muscular fatigue determiner that, if the difference between the myoelectric potentials obtained by the myoelectric potential comparer is larger than the first threshold, determines that muscular fatigue has occurred.

According to this aspect, the myoelectric potential comparer can always compare a myoelectric potential obtained by the myoelectric potential obtainer with a first myoelectric potential in a state in which muscular fatigue has not occurred, and the accuracy of determining presence or absence of muscular fatigue or the level of muscular fatigue can be increased.

According to an eighth aspect of the present disclosure, the muscular fatigue determination apparatus according to the seventh aspect is provided in which, when comparing the myoelectric potentials in the same load group with each other, the muscular fatigue information generator uses a load group for largest loads among the plurality of load groups into which the loads have been classified by the load classifier.

According to this aspect, because, after muscular fatigue occurs, a change in myoelectric potential in a group in which loads are higher is larger than a change in myoelectric potential in a group in which loads are lower, the myoelectric potential obtainer can avoid a possible error by using the change in myoelectric potential in the group in which the loads are higher. As a result, the accuracy of determining presence or absence of muscular fatigue or the level of muscular fatigue can be increased.

According to a ninth aspect of the present disclosure, the muscular fatigue determination apparatus according to the seventh aspect is provided in which, if generating muscular fatigue information regarding the user indicating that muscular fatigue has occurred, the muscular fatigue information generator calculates a difference between the myoelectric potentials in the same load group and the first threshold as a level of muscular fatigue and outputs the level of muscular fatigue.

According to this aspect, the muscular fatigue determiner can not only determine presence or absence of muscular fatigue but also quantify the muscular fatigue.

According to a tenth aspect of the present disclosure, a method for determining muscular fatigue is provided. The method includes obtaining, with an information obtainer, loads, rotation speeds, and myoelectric potentials of a user, using a load detector that detects the loads applied to a pedal of a bicycle, a rotation speed detector that detects the rotation speeds of a crank of the bicycle, and a myoelectric potential detector that detects the myoelectric potentials, the myoelectric potentials and the loads being in a one-to-one relationship, the myoelectric potentials and the rotation speeds being in a one-to-one relationship, and generating, with a muscular fatigue information generator, muscular fatigue information regarding the user on the basis of whether a difference between the myoelectric potentials of the user is larger than a first threshold, each of the myoelectric potentials of the user being associated to a load range that is one of load ranges and to a rotation speed range that is one of rotation speed ranges, each of the loads belonging to one of the load ranges and each of the rotation speed ranges belonging to one of the rotation speed ranges.

According to this aspect, muscular fatigue information regarding the user can be generated, without performing calibration in advance, on the basis of a relationship between the load applied to the pedal, the rotation speed of the crank, and the myoelectric potential of the user while the user is rotating the crank by stepping on the pedal of a bicycle or a cycle trainer, and presence or absence of muscular fatigue or a level of muscular fatigue can be determined in real-time.

According to an eleventh aspect of the present disclosure, a recording medium storing a control program for causing a device including a processor to execute a process is provided, the recording medium being a nonvolatile computer-readable recording medium. The process includes obtaining loads applied to a pedal of a bicycle, rotation speeds of a crank of the bicycle, and myoelectric potentials of a user, the myoelectric potentials and the loads being in a one-to-one relationship, the myoelectric potentials and the rotation speeds being in a one-to-one relationship, and generating muscular fatigue information regarding the user on the basis of whether a difference between the myoelectric potentials of the user is larger than a first threshold, each of the myoelectric potentials of the user being associated to a load range that is one of load ranges and to a rotation speed range that is one of rotation speed ranges, each of the loads belonging to one of the load ranges and each of the rotation speed ranges belonging to one of the rotation speed ranges.

According to this aspect, muscular fatigue information regarding the user can be generated, without performing calibration in advance, on the basis of a relationship between the load applied to the pedal, the rotation speed of the crank, and the myoelectric potential of the user while the user is rotating the crank by stepping on the pedal of a bicycle or a cycle trainer, and presence or absence of muscular fatigue or a level of muscular fatigue can be determined in real-time.

According to a twelfth aspect of the present disclosure, a method for determining muscular fatigue is provided. The method includes obtaining first information based on a first myoelectric potential difference of a user who is rotating a crank, at a first rotation speed, connected to a pedal of a bicycle by applying first force to the pedal and second information based on a second myoelectric potential difference of the user who is rotating the crank, at a second rotation speed, by applying second force to the pedal, obtaining third information based on the first force or first torque applied to a crank axle on the basis of the first force and fourth information based on the second force or second torque applied to the crank axle on the basis of the second force, obtaining fifth information based on the first rotation speed and sixth information based on the second rotation speed, and comparing seventh information with eighth information if the third information and the forth information belong to the same category among a plurality of categories. Each of the plurality of categories is defined on the basis of a predetermined force or torque range. The first information is corrected to the seventh information on the basis of the third information and the fifth information, the seventh information becoming smaller as the fifth information becomes larger. The second information is corrected to the eighth information on the basis of the fourth information and the sixth information the eighth information becoming smaller as the sixth information becomes larger.

According to a thirteenth aspect of the present disclosure, the method according to the twelfth aspect is provided in which an electromyograph attached to the user detects the first myoelectric potential difference and the second myoelectric potential difference. A rotation speed sensor mounted on the bicycle detects the first rotation speed and the second rotation speed. A force sensor mounted on the bicycle detects the first force and the second force. A torque sensor mounted on the bicycle detects the first torque and the second torque.

An embodiment of the present disclosure will be described in detail hereinafter with reference to the drawings.

A muscular fatigue determination apparatus according to an embodiment of the present disclosure will be described in detail.

A muscular fatigue determination apparatus 392 at least includes the information obtaining unit 400 and the muscular fatigue information generation unit 399 (refer to FIG. 5) and can determine muscular fatigue in real-time while the user 100 is pedaling a bicycle or the cycle trainer (hereinafter referred to as a bicycle as an example) 104.

The information obtaining unit 400 associates a load applied to the pedal 103 of the bicycle 104 obtained by a load sensor 401a, the rotation speed of the crank 105 obtained by a rotation speed sensor 402a, and the myoelectric potential of the user 100 obtained by an electromyograph 403a corresponding to the load applied to the pedal 103 and the rotation speed with one another.

The information obtaining unit 400 obtains a load applied to the pedal 103 of the bicycle 104, the rotation speed of the crank 105, and the myoelectric potential of the user 100 corresponding to the load applied to the pedal 103 and the rotation speed. More specifically, the information obtaining unit 400 may associate a load, a rotation speed, and a myoelectric potential with a point of time, that is, for example, the information obtaining unit 400 may associate a load fi, a rotation speed ui, and a myoelectric potential vi with a time ti.

The muscular fatigue information generation unit 399 generates muscular fatigue information regarding the user 100 on the basis of whether a difference between a plurality of myoelectric potentials associated with loads obtained by the information obtaining unit 400 and rotation speeds obtained by the information obtaining unit 400 within certain ranges (e.g., ranges of values of groups that will be described later) is larger than a first threshold (a muscular fatigue threshold that will be described later). More specifically, the muscular fatigue information generation unit 399 compares myoelectric potentials at different times whose loads and rotation speeds are close to each other. In other words, the muscular fatigue information generation unit 399 compares myoelectric potentials whose loads and rotation speeds are close to each other. The muscular fatigue information generation unit 399 generates muscular fatigue information regarding the user 100 through such a comparison. If the information obtaining unit 400 has obtained loads, rotation speeds, and myoelectric potentials associated with points of time, the muscular fatigue information generation unit 399 compares myoelectric potentials at different times whose loads and rotation speeds are close to each other to generate muscular fatigue information regarding the user 100.

Loads or rotation speeds can be said to be close to each other when loads or rotation speeds belong to the same load or rotation speed group among a plurality of load or rotation speed groups for different ranges of values. In other words, loads belong to the same load group among the plurality of load groups for different ranges of values or rotation speeds belong to the same rotation speed among the plurality of rotation speed groups for different ranges of values.

That is, if there are a myoelectric potential vi, a load fi, and a rotation speed ui at a time ti and a myoelectric potential vj, a load fj, and a rotation speed uj at a time tj, the loads fi and fj belong to the same load group and the rotation speeds ui and uj belong to the same rotation speed group when the loads fi and fj and the rotation speeds ui and uj associated with the myoelectric potentials vi and vj at different times are close to each other. The myoelectric potentials, the loads, and the rotation speeds refer to values of the myoelectric potentials, the loads, and the rotation speeds, respectively.

The load fi or fj, for example, belongs to one of four load groups in accordance with the value thereof. The four load groups may be a first load group including loads equal to or higher than fa but lower than fb, a second load group including loads equal to or higher than fb but lower than fc, a third load group including loads equal to or higher than fc but lower than fd, and a fourth load group including loads equal to or higher than fd but lower than fe. Here, fa<fb<fc<fd<fe. The load fi or fj may be torque or force. The load groups may be torque groups including values of torque or force groups including values of force.

The rotation speed ui or uj, for example, belongs to one of three rotation speed groups in accordance with the value thereof. The three rotation speed groups may be a first rotation speed group including rotation speeds equal to or higher than ua but lower than ub, a second rotation speed group including rotation speeds equal to or higher than ub but lower than uc, and a third rotation speed group including rotation speeds equal to or higher than uc but lower than ud. Here, ua<ub<uc<ud.

If the load fi is equal to or larger than fa but smaller than fb, that is, the load fi belongs to the first load group, and the rotation speed ui is equal to or higher than ub but lower than uc, that is, the rotation speed ui belongs to the second rotation speed group, the load fj is equal to or larger than fa but smaller than fb and the rotation speed uj is equal to or higher than ub but lower than uc when the loads fi and fj and the rotation speeds ui and uj associated with the myoelectric potentials vi and vj at different times are close to each other.

The muscular fatigue information generation unit 399 classifies, for example, a load applied to the pedal 103 and the rotation speed of the crank 105 into one of the plurality of load groups and one of the plurality of rotation speed groups, respectively, on the basis of information obtained by the information obtaining unit 400 and stores a myoelectric potential associated with the load and the rotation speed in a storage unit 405, which will be described later. The muscular fatigue information generation unit 399 can determine presence or absence of muscular fatigue or a level of muscular fatigue on the basis of a difference between a newly measured myoelectric potential and a myoelectric potential stored in the storage unit 405 whose loads belong to the same load group and rotation speeds belong to the same rotation speed group.

Figure 5:
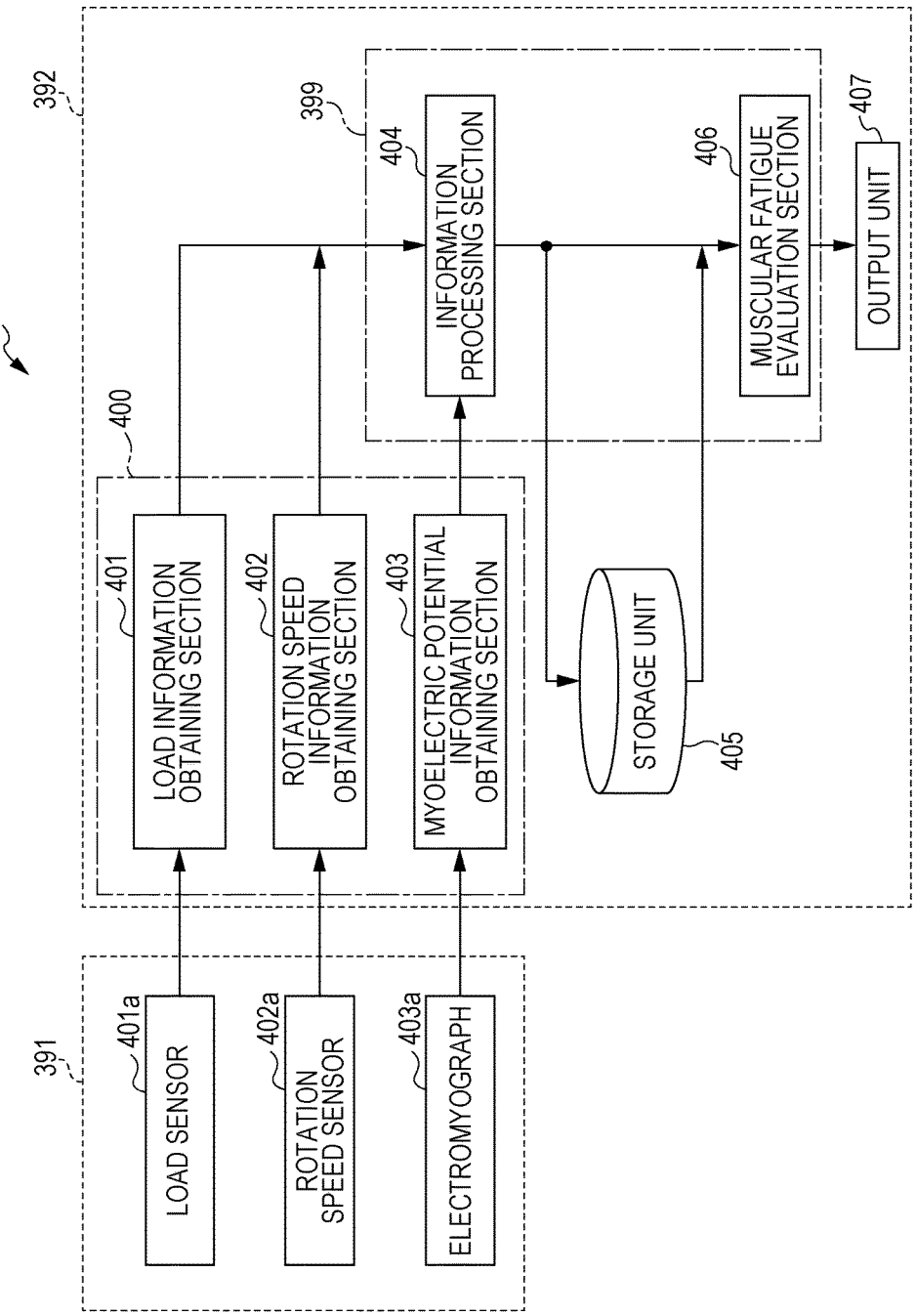
FIG. 5 is a block diagram illustrating a muscular fatigue determination system including a muscular fatigue determination apparatus according to an embodiment of the present disclosure.

FIG. 5 is a block diagram illustrating the configuration of a muscular fatigue determination system 390. The muscular fatigue determination system 390 includes external sensors 391 and the muscular fatigue determination apparatus 392 according to the embodiment of the present disclosure. The muscular fatigue determination apparatus 392 may include the external sensors 391, instead.

The external sensors 391 include the load sensor 401a, which is an example of a load measuring unit, the rotation speed sensor 402a, which is an example of a rotation speed measuring unit, and the electromyograph 403a, which is an example of a myoelectric potential measuring unit. Each sensor obtains a value and outputs the value to the muscular fatigue determination apparatus 392.

The muscular fatigue determination apparatus 392 obtains measurement signals from the external sensors 391 and determines muscular fatigue. The muscular fatigue determination apparatus 392 at least includes the information obtaining unit 400 and the muscular fatigue information generation unit 399. More specifically, the muscular fatigue determination apparatus 392 includes the information obtaining unit 400 (a load information obtaining section 401, a rotation speed information obtaining section 402, and a myoelectric potential information obtaining section 403), the muscular fatigue information generation unit 399 (an information processing section 404 and a muscular fatigue evaluation section 406), the storage unit 405, and an output unit 407. The information obtaining unit 400 includes the load information obtaining section 401, the rotation speed information obtaining section 402, and the myoelectric potential information obtaining section 403. The muscular fatigue information generation unit 399 includes the information processing section 404 and the muscular fatigue evaluation section 406.

The load sensor 401a is, for example, provided for one of pedals of the bicycle 104, measures a load (load information) applied to the pedal 103, and outputs the measured information to the load information obtaining section 401 of the muscular fatigue determination apparatus 392. The load may be a value of torque applied to the crank axle 110 of the bicycle 104, a value of total force applied to the pedals, or a value of force applied to the pedal 103. In the following description, a case will be described in which the load sensor 401a is provided only for one of the pedals, in order to simplify the description. The present disclosure, however, is not limited to this. If load sensors 401a are provided for both the pedals, myoelectric potentials of left and right rectus femoris muscles can be separately measured, and muscular fatigue can be determined for each leg.

The load sensor 401a may include a distortion sensor that is provided near the crank axle 110 and that detects the amount of distortion and a calculator that calculates torque applied by the user or subject 100 of the bicycle 104 to the bicycle 104 on the basis of the detected amount of distortion.

The rotation speed sensor 402a is, for example, provided for the pedal 103 like the rotation speed sensor 102 illustrated in FIG. 1B, measures the rotation speed (rotation speed information) of the crank 105, and outputs the measured information to the rotation speed information obtaining section 402 of the muscular fatigue determination apparatus 392.

The electromyograph 403a measures a potential difference between a plurality of electrodes attached to the user 100 as the myoelectric potential of the user 100. In an example, as in the above-described experiments, a plurality of electrodes are attached to the rectus femoris muscle of the user 100 (for example, refer to FIG. 1A). The electromyograph 403a measures the potential difference between the plurality of electrodes as the myoelectric potential (myoelectric potential information) of the rectus femoris muscle of the user 100 and outputs the measured information to the myoelectric potential information obtaining section 403 of the muscular fatigue determination apparatus 392. The electromyograph 403a may include an RMS calculator that calculates an RMS of myoelectric potentials from measured potential differences between the plurality of electrodes. The RMS calculator calculates an RMS from potential differences in a certain period.

The muscular fatigue determination apparatus 392 includes the information processing section 404 that processes all of obtained data. The storage unit 405 is used for storing results of the processing performed by the information processing section 404. Details of the information processing section 404 will be described later.

The muscular fatigue evaluation section 406 compares latest data processed by the information processing section 404 and data stored in the storage unit 405 (e.g., data stored at a beginning of pedaling) to evaluate muscular fatigue information. A specific comparison method used will be described later. The output unit 407 receives a result of the evaluation made by the muscular fatigue evaluation section 406 and outputs the result. The muscular fatigue evaluation section 406 need not always compare a latest result with data stored in the storage unit 405. The muscular fatigue evaluation section 406 may use, for example, an average of last three myoelectric potentials, instead, in order to minimize an error.

Figure 6:
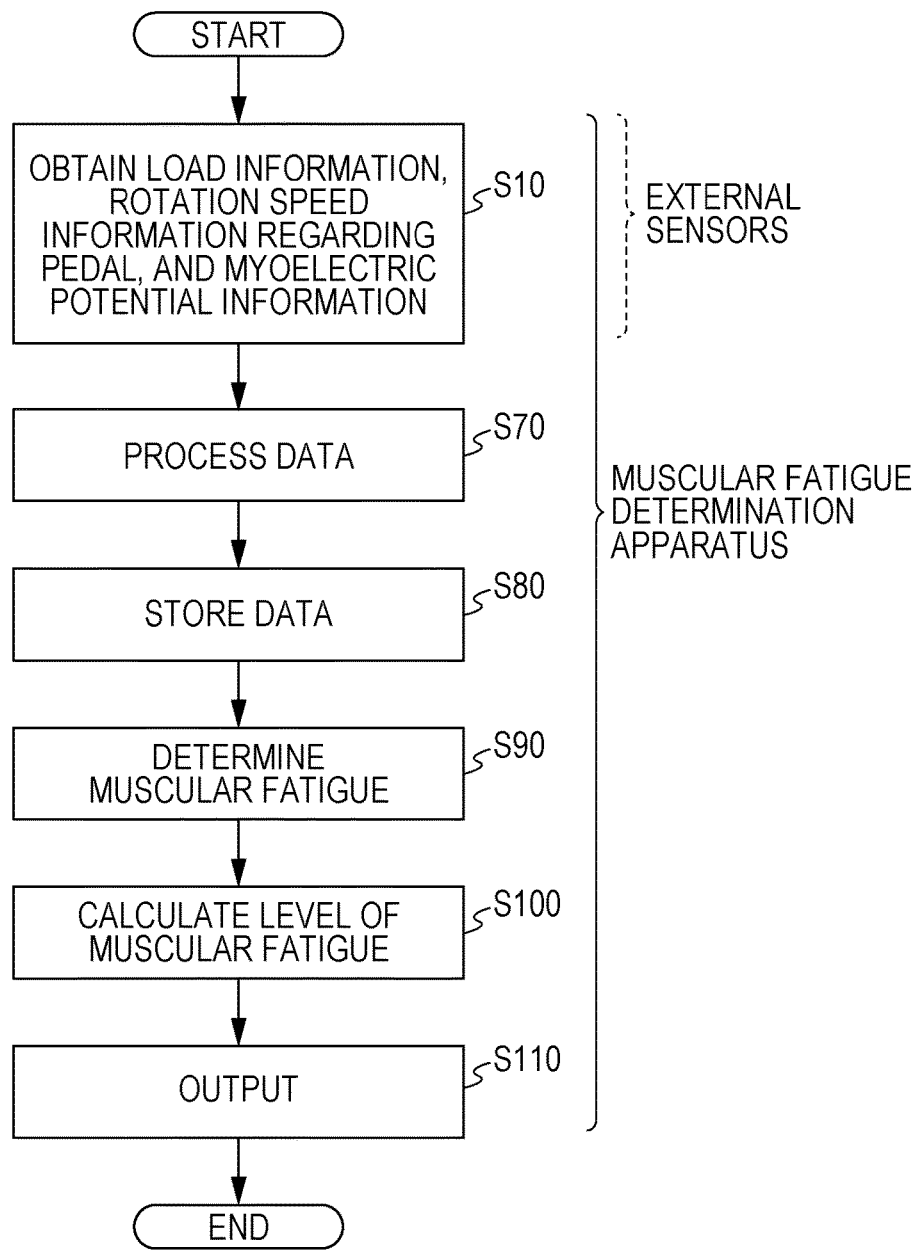
FIG. 6 is a flowchart illustrating a process performed by the muscular fatigue determination system.

Next, an overall process performed by the muscular fatigue determination system 390 will be described with reference to a flowchart of FIG. 6. In particular, processing performed by the information obtaining unit 400 and processing performed by the information processing section 404 will be described in detail.

First, in step S10, load information, rotation speed information regarding the crank 105, and myoelectric potential information are associated with a point of time and obtained by the information obtaining unit 400, that is, the load information obtaining section 401, the rotation speed information obtaining section 402, and the myoelectric potential information obtaining section 403, respectively. The load, the rotation speed, and the myoelectric potential are associated with one another on the basis of the point of time. If the load information obtaining section 401, the rotation speed information obtaining section 402, and the myoelectric potential information obtaining section 403 obtain these pieces of information at certain time intervals (e.g., every 30 seconds or 1 minute), for example, the pieces of information can be easily associated with one another. Each of operations performed in step S10 will be described in detail hereinafter.

Figure 7:
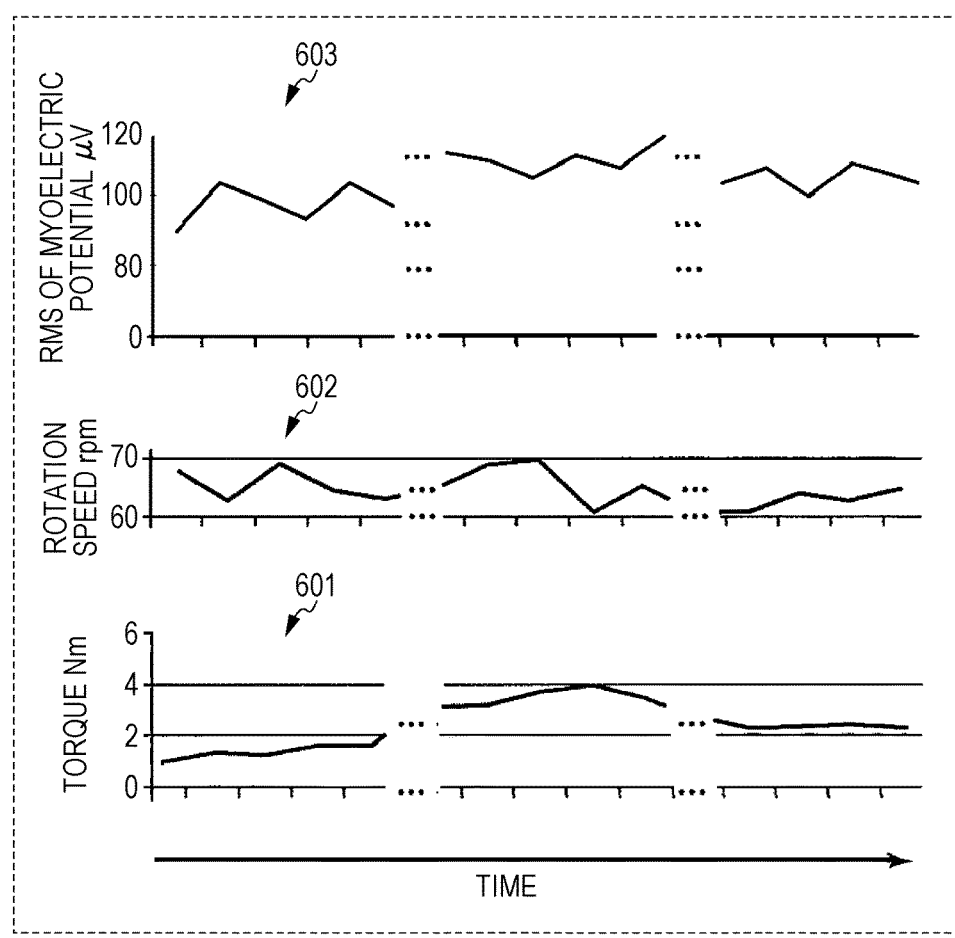
FIG. 7 is a diagram illustrating an outline of data measured by the muscular fatigue determination system.

First, a load measured by the load sensor 401a is associated with a point of time, output to the load information obtaining section 401 of the muscular fatigue determination apparatus 392, and obtained by the load information obtaining section 401 as load information. More specifically, the load sensor 401a mounted on the pedal 103 of the bicycle 104 measures a load applied to the crank 105 and outputs the measured load to the load information obtaining section 401 of the muscular fatigue determination apparatus 392 while associating the load with a point of time. The load information obtaining section 401 obtains the load as load information. Time intervals at which load information is output may be adjusted. Here, for example, the sum or an average of torque values is calculated after the crank 105 makes one rotation from a top position and output from the load sensor 401a while being associated with a point of time. The load information obtaining section 401 obtains the sum or the average of torque values as load information. FIG. 7 illustrates an outline of load information (e.g., torque values and points of time) 601 output from the load sensor 401a to the load information obtaining section 401. In this example of load information, torque values and points of time are associated with each other.

The rotation speed sensor 402a associates a measured rotation speed of the crank 105 with a point of time and outputs the rotation speed to the rotation speed information obtaining section 402 of the muscular fatigue determination apparatus 392 as rotation speed information. The rotation speed information obtaining section 402 obtains the output rotation speed information. FIG. 7 illustrates an outline of rotation speed information 602 output from the rotation speed sensor 402a to the rotation speed information obtaining section 402. In this example of rotation speed information, rotation speeds and points of time are associated with each other.

The electromyograph 403a associates a measured myoelectric potential of the user 100 with a point of time and outputs the myoelectric potential to the myoelectric potential information obtaining section 403 of the muscular fatigue determination apparatus 392 as myoelectric potential information. The myoelectric potential information obtaining section 403 obtains the output myoelectric potential information. FIG. 7 illustrates an outline of myoelectric potential information 603 in which myoelectric potentials measured by the electromyograph 403a are associated with points of time. In this example of myoelectric potential information, myoelectric potentials and points of time are associated with each other. The myoelectric potentials included in the myoelectric potential information are measured potential differences between a plurality of electrodes or an RMS.

The load sensor 401a, the rotation speed sensor 402a, and the electromyograph 403a may associate load information, rotation speed information, and myoelectric potential information, respectively, with a point of time at predetermined time intervals and output the load information, the rotation speed information, and the myoelectric potential information. The load sensor 401a, the rotation speed sensor 402a, and the electromyograph 403a output the load information, the rotation speed information, and the myoelectric potential information after the crank 105 makes one rotation from the top position. The myoelectric potential information 603, the rotation speed information 602, and the load information 601 illustrated in FIG. 7 are synchronized with one another.

Next, in step S70, the load information obtaining section 401, the rotation speed information obtaining section 402, and the myoelectric potential information obtaining section 403 output the obtained data to the information processing section 404, and the information processing section 404 analyzes the data. Details of the analysis of the data conducted by the information processing section 404 will be described later with reference to FIG. 9.

Next, in step S80, information regarding a result of the processing performed by the information processing section 404 is stored in the storage unit 405.

Next, in step S90, the muscular fatigue evaluation section 406 compares the information regarding the latest result of the processing performed by the information processing section 404 with data (information) stored in the storage unit 405 to generate muscular fatigue information including determination information indicating whether muscular fatigue has occurred. If a difference between results is equal to or larger than a certain threshold, for example, the muscular fatigue evaluation section 406 determines that muscular fatigue has occurred in the user 100. If the muscular fatigue evaluation section 406 determines that muscular fatigue has occurred, a muscular fatigue occurrence time is output. The muscular fatigue information at least includes either information indicating presence or absence of muscular fatigue or information indicating the level of muscular fatigue. A specific process will be described later with reference to FIG. 9.

Next, in step S100, if the muscular fatigue evaluation section 406 has determined in step S90 that muscular fatigue has occurred, the muscular fatigue evaluation section 406 calculates the level of muscular fatigue and outputs a result of the calculation to the output unit 407. A method for calculating the level of muscular fatigue will be described later with reference to FIG. 11.

Next, in step S110, the output unit 407 outputs information regarding a result obtained by the muscular fatigue evaluation section 406. Presence or absence of occurrence of muscular fatigue (a time at which muscular fatigue has occurred) or the level of muscular fatigue, for example, may be output to an external device (a display device or the like) as an example of the output unit 407 and displayed. Alternatively, an external device (an arithmetic unit or the like) may perform another process.

Although the information obtaining unit 400 obtains a load, a rotation speed, and a myoelectric potential associated with a point of time in step S10, a load, a rotation speed, or a myoelectric potential obtained by the information obtaining unit 400 need not necessarily be associated with a point of time. The information obtaining unit 400 may at least obtain a load, a rotation speed, and a myoelectric potential corresponding to the load and the rotation speed. In an example, a time at which the muscular fatigue evaluation section 406 has determined in step S90 that muscular fatigue has occurred in the user 100 is output as a muscular fatigue occurrence time.

Data Processing

Figure 8:
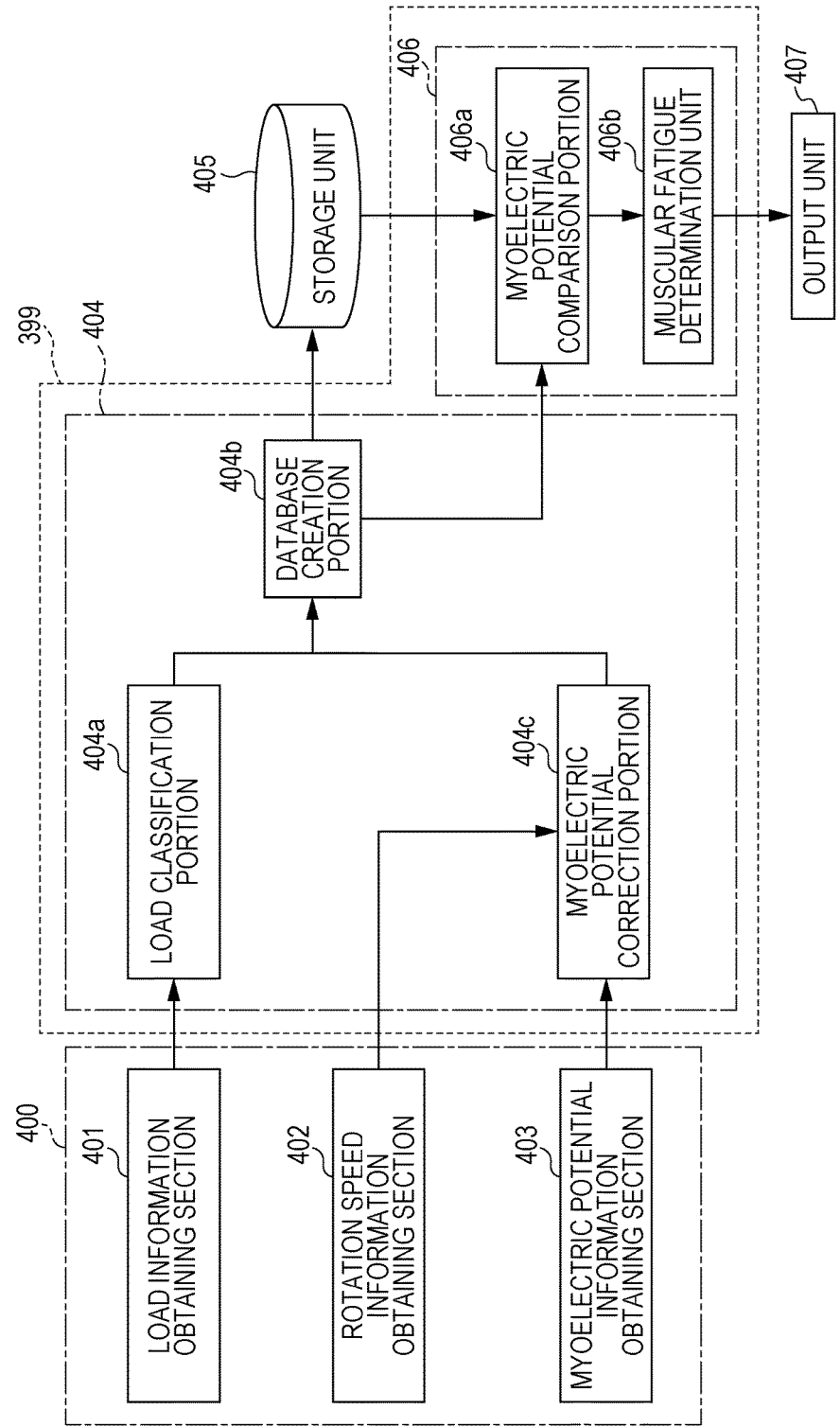
FIG. 8 is a block diagram illustrating details of the muscular fatigue determination apparatus.

FIG. 8 is a block diagram illustrating details of the muscular fatigue determination apparatus 392 illustrated in FIG. 5.

The information processing section 404 includes a load classification portion (classification portion) 404a, a database creation portion 404b, and a myoelectric potential correction portion 404c.

The load classification portion 404a receives load information obtained by the load information obtaining section 401. The load classification portion 404a prepares two or more load groups for different ranges of values and classifies a load included in the received load information into one of the two or more load groups in accordance with a value of the load. The load classification portion 404a also prepares two or more rotation speed groups for different ranges of values and classifies a rotation speed included in received rotation speed information into one of the two or more rotation speed groups in accordance with a value of the rotation speed. The load classification portion 404a then outputs the load information, group information regarding the load information, the rotation speed information, and group information regarding the rotation speed information to the database creation portion 404b. The load classification portion 404a may at least prepare two or more load groups for different ranges of values and classify a load included in received load information into one of the two or more load groups in accordance with a value of the load. The load classification portion 404a might not classify rotation speeds in order to simplify the muscular fatigue determination system 390. In this case, the load classification portion 404a outputs load information and group information regarding the load information to the database creation portion 404b. A range of values of each group into which a load or a rotation speed is classified may be arbitrarily determined.

The more the number of load groups or rotation speed groups, the higher the accuracy of determining muscular fatigue. The more the number of groups, however, the more complex the configuration of the muscular fatigue determination system 390. In the present embodiment, for example, the number of load groups is 4.

More specifically, if a load in the present embodiment is represented by torque (unit: newton meter (N·m)), four load groups are prepared while setting 4 N·m, which is considerably high, as a highest torque.

Similarly, if a rotation speed is expressed in rpm, three rotation speed groups are prepared while setting 100 rpm, which is considerably high, as a highest rotation speed. Although the highest rotation speed is 100 rpm here, a higher rotation speed may be used as the highest rotation speed. A reference rotation speed is usually 60 to 80 rpm in actual pedaling.

The myoelectric potential correction portion 404c receives rotation speed information obtained by the rotation speed information obtaining section 402 and myoelectric potential information obtained by the myoelectric potential information obtaining section 403. The myoelectric potential correction portion 404c corrects the myoelectric potential information using the rotation speed information and outputs information obtained as a result of the correction to the database creation portion 404b.

The database creation portion 404b creates a database on the basis of information from the load classification portion 404a and the myoelectric potential correction portion 404c and information regarding points of time and outputs the database to the storage unit 405 and a myoelectric potential comparison portion 406a of the muscular fatigue evaluation section 406. In FIG. 10, there are four load groups, and three rotation speed groups are included in each load group.

The muscular fatigue evaluation section 406 includes the myoelectric potential comparison portion 406a and the muscular fatigue determination unit 406b.

The myoelectric potential comparison portion 406a receives the database created by the database creation portion 404b and stored in the storage unit 405, a load included in latest load information and information regarding a load group to which the latest load information belongs input to the database creation portion 404b, and a rotation speed included in latest rotation speed information and information regarding a rotation speed group to which the latest rotation speed information belongs input to the database creation portion 404b. The myoelectric potential comparison portion 406a obtains a difference (a change in the RMS of myoelectric potentials) between a first RMS of myoelectric potentials (e.g., immediately after a beginning of pedaling) belonging to the same load group as latest load information among the plurality of load groups in the database and the same rotation speed group as latest rotation speed information and an RMS of myoelectric potentials included in latest myoelectric potential information and outputs the difference to the muscular fatigue determination unit 406b. In short, the myoelectric potential comparison portion 406a may compare myoelectric potentials obtained at different times. If a latest RMS of myoelectric potentials is used, latest muscular fatigue can be determined, and if myoelectric potentials 5 minutes ago is used, for example, muscular fatigue 5 minutes ago can be determined. The myoelectric potential comparison portion 406a need not necessarily compare a latest RMS of myoelectric potentials with an RMS of myoelectric potentials immediately after the beginning of pedaling. The myoelectric potential comparison portion 406a may use an RMS of myoelectric potentials temporally close to the latest RMS of myoelectric potentials, instead, in order to minimize an error. Alternatively, an average of myoelectric potentials in a certain period of time, namely, for example, 30 seconds, may be used instead of an RMS of myoelectric potentials.

The muscular fatigue determination unit 406b sets in advance a muscular fatigue threshold for each rotation speed group and receives a difference between myoelectric potentials from the myoelectric potential comparison portion 406a. The muscular fatigue determination unit 406b compares the difference between myoelectric potentials with the muscular fatigue threshold and, if the difference between myoelectric potentials is larger than the muscular fatigue threshold, determines that muscular fatigue has occurred. The muscular fatigue determination unit 406b then determines a determination time as a muscular fatigue time. The muscular fatigue determination unit 406b also calculates the level of muscular fatigue and outputs the result of the determination and the level of muscular fatigue to the output unit 407. If the difference between myoelectric potentials is equal to or smaller than the muscular fatigue threshold, the muscular fatigue determination unit 406b determines that muscular fatigue has not occurred. In this case, the muscular fatigue determination unit 406b may or may not output the result of the determination, that is, information indicating that muscular fatigue has not occurred, to the output unit 407.

The muscular fatigue determination unit 406b may determine that muscular fatigue has occurred once a difference between myoelectric potentials becomes larger than the muscular fatigue threshold. In order to minimize an error, however, the muscular fatigue determination unit 406b may determine that muscular fatigue has occurred only after differences between myoelectric potentials remain larger than the muscular fatigue threshold for a certain period of time.

Next, steps S70 and S100 in the flowchart of FIG. 6 will be described in more details with reference to the block diagram of FIG. 8 and a flowchart of FIG. 9.

Figure 9:
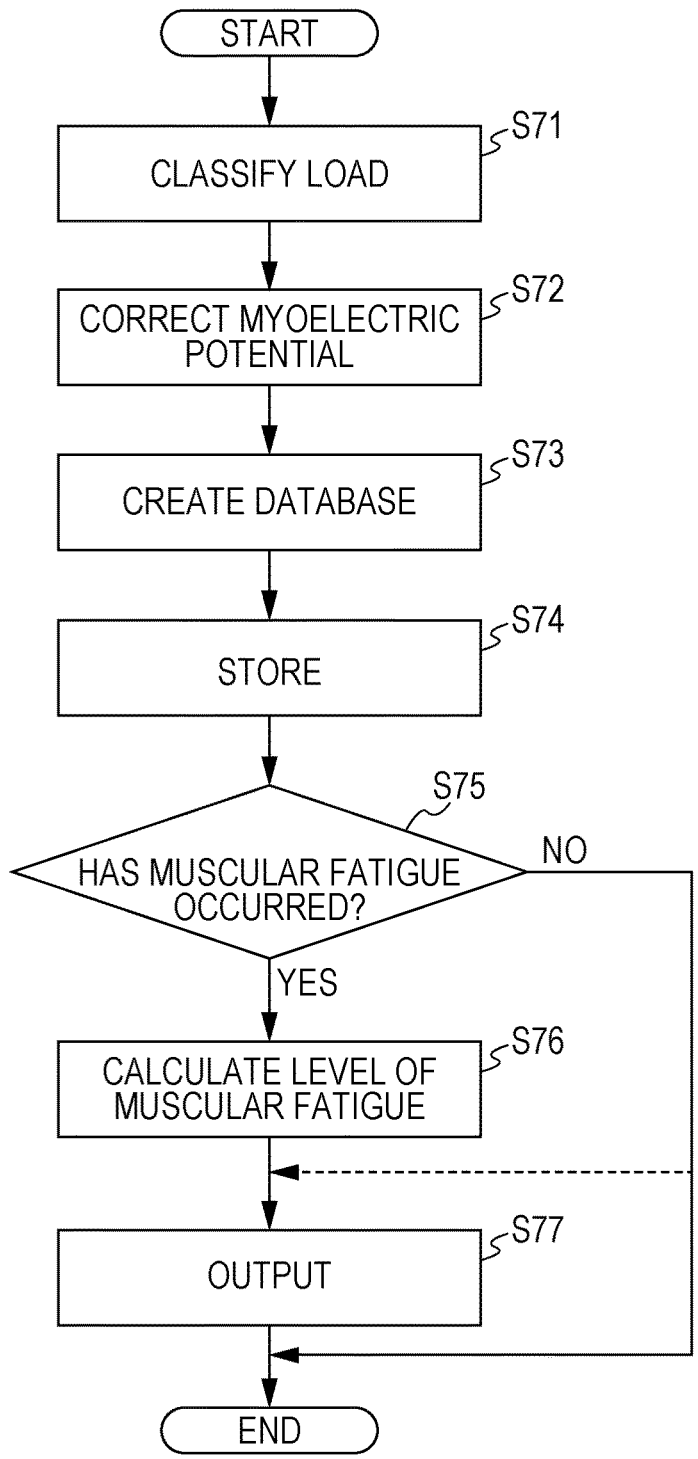
FIG. 9 is a flowchart illustrating data processing performed by the muscular fatigue determination apparatus.

The data analysis conducted by the information processing section 404 in step S70 includes, for example, steps S71 to S77 as illustrated in FIG. 9.

First, in step S71, the load classification portion 404a classifies a load obtained from the load information obtaining section 401. If a torque value is treated as a load, the load classification portion 404a prepares a plurality of load groups for different ranges of values such as 0 to 1 N·m, 1 to 2 N·m, 2 to 3 N·m, and 3 N·m or more. The load classification portion 404a then classifies the load obtained by the load information obtaining section 401 into one of the load groups on the basis of the value of the load. The load classification portion 404a outputs load information and information regarding a group to which the load information belongs to the database creation portion 404b.

Next, in step S72, the myoelectric potential correction portion 404c corrects myoelectric potential information obtained from the myoelectric potential information obtaining section 403. As a result of the above-described experiments, it is known that a resultant myoelectric potential differs depending on the rotation speed of the crank 105 even if the user 100 pedals the bicycle 104 with the same load (refer to FIGS. 3A to 3D). If the myoelectric potential correction portion 404c corrects the myoelectric potential on the basis of the rotation speed, therefore, the accuracy of estimating muscular fatigue is expected to improve. A rotation speed group for 60 to 79 rpm, for example, is predetermined as a reference rotation speed group, and if an obtained rotation speed is higher than the reference rotation speed, the information processing section 404c decreases a corresponding myoelectric potential. If, on the other hand, an obtained rotation speed is lower than the reference rotation speed, the myoelectric potential correction portion 404c increases a corresponding myoelectric potential. That is, in this correction, if a rotation speed corresponding to a measured myoelectric potential is different from the reference rotation speed, a myoelectric potential corresponding to the reference rotation speed is obtained. Details of this process will be described hereinafter. Correction coefficients used by the myoelectric potential correction portion 404c to correct myoelectric potentials are obtained in advance through experiments. FIG. 11A illustrates, for example, correction coefficients for myoelectric potentials based on the load groups and the rotation speeds.

FIG. 10 is a diagram illustrating stored data before feature values of myoelectric potentials are corrected. First, the load classification portion 404a classifies an obtained load into a load group and then classifies a rotation speed obtained by the rotation speed information obtaining section 402 into a rotation speed group. More specifically, if the obtained load (e.g., torque) is low (e.g., if the torque is equal to or lower than 1 N·m), the load classification portion 404a classifies the load into load group 1. If the obtained load is high (e.g., if the torque is 3 N·m or higher), the load classification portion 404a classifies the load into load group 4. Next, in load group 1, the rotation speed obtained by the rotation speed information obtaining section 402 is classified into a rotation speed group for 40 to 59 rpm, a rotation speed group for 60 to 79 rpm, or a rotation speed group for 80 to 100 rpm, for example, and an RMS of myoelectric potentials is stored in the rotation speed group at certain intervals (e.g., 30 seconds). Myoelectric potentials obtained by the myoelectric potential information obtaining section 403 are sequentially classified into groups in this manner and stored in the storage unit 405. When RMSs of myoelectric potentials are compared with each other, the RMSs need to belong to the same load group and the same rotation speed group. As described above, in order to simplify the process for comparing data, the myoelectric potential correction portion 404c may correct an obtained rotation speed to the reference rotation speed using one of the correction coefficients illustrated in FIG. 11A and then classify a load into a load group.

The correction coefficients illustrated in FIG. 11A will be described. Even when the load remains the same during pedaling, an RMS of myoelectric potentials increases if the rotation speed increases or decreases if the rotation speed decreases. A range of reference rotation speeds is determined in advance, and if an obtained rotation speed falls below the range of reference rotation speeds, an RMS of myoelectric potentials needs to be increased. If an obtained rotation speed exceeds the range of reference rotation speeds, an RMS of myoelectric potentials needs to be decreased. More specifically, in FIG. 11A, the range of reference rotation speeds is determined as 60 to 79 rpm, for example, and if an obtained rotation speed falls below the range (40 to 59 rpm), a correction coefficient larger than 1 is used to increase an RMS of myoelectric potentials. If an obtained rotation speed exceeds the range of reference rotation speeds (80 to 100 rpm), a correction coefficient smaller than 1 is used to decrease an RMS of myoelectric potentials. The correction coefficient used for increasing or decreasing an RMS of myoelectric potentials also differs depending on the load, that is, if the load becomes higher, the correction coefficient becomes larger. The correction coefficients are obtained in advance through experiments.

In this correction method, if an obtained rotation speed is within the range of reference rotation speeds, the myoelectric potential correction portion 404c multiplies an RMS of myoelectric potentials by 1 as a correction coefficient (that is, the RMS remains the same). If an obtained rotation speed is within a range of 40 to 59 rpm, the myoelectric potential correction portion 404c multiplies an obtained RMS of myoelectric potentials by a correction coefficient in a "40 59" column illustrated in FIG. 11A for a corresponding load group. Similarly, if an obtained rotation speed is within a range of 80 to 100 rpm, the myoelectric potential correction portion 404c multiplies an obtained RMS of myoelectric potentials by a correction coefficient in a "80→100" column illustrated in FIG. 11A for a corresponding load group.

Next, in step S73, the database creation portion 404b of the information processing section 404 creates a database from the load group for the RMS of myoelectric potentials corrected by the myoelectric potential correction portion 404c and outputs the database to the storage unit 405 to store the database. FIG. 11B illustrates the database that has been created by the database creation portion 404b and in which RMSs of myoelectric potentials have been corrected.

Next, in step 374, the storage unit 405 sequentially receives data created by the database creation portion 404b, and the data is sequentially stored in the database.

Next, in step 375, the muscular fatigue evaluation section 406 compares data in the database stored in the storage unit 405 with an RMS of myoelectric potentials included in latest data created by the database creation portion 404b to determine whether muscular fatigue has occurred. In an example of the process for comparing data, the muscular fatigue evaluation section 406 obtains an average of last three RMSs of myoelectric potentials and then obtains a difference between the average and a first value in the same load group. Alternatively, in order to eliminate a possible error in the first value, an average of first two or three values may be obtained as the first value. Similarly, in order to eliminate a possible error in a latest value, an average of last two or three values may be obtained as the latest value.

The myoelectric potential comparison portion 406a obtains a difference (a change in the RMS of myoelectric potentials) between a first RMS of myoelectric potentials and a latest RMS of myoelectric potentials in the same load group and outputs the difference to the muscular fatigue determination unit 406b. If the difference between the RMSs of the myoelectric potentials is larger than the muscular fatigue threshold, the muscular fatigue determination unit 406b determines that muscular fatigue has occurred. The muscular fatigue determination unit 406b then determines a determination time as a muscular fatigue time and outputs the muscular fatigue time to the output unit 407. If the difference between the RMSs of myoelectric potentials is equal to or smaller than the muscular fatigue threshold, the muscular fatigue determination unit 406b determines that muscular fatigue has not occurred. If muscular fatigue has not occurred, the process for comparing data using this comparison method ends.

FIG. 11B illustrates an example of occurrence of muscular fatigue F1. Because a change in the RMS of myoelectric potentials is larger than the muscular fatigue threshold (the muscular fatigue threshold is 30 in this specific example of the present embodiment), the muscular fatigue determination unit 406b determines that muscular fatigue has occurred and then calculates the level of muscular fatigue. The level of muscular fatigue will be described hereinafter with reference to step S76.

In step S76, which is performed if the muscular fatigue determination unit 406b determines in step S75 that muscular fatigue has occurred, the muscular fatigue determination unit 406b calculates the level of muscular fatigue. In an example of a method for calculating the level of muscular fatigue, the muscular fatigue determination unit 406b calculates a ratio of the difference described with reference to with step S75 to the muscular fatigue threshold as the level of muscular fatigue (refer to FIG. 11B). More specifically, the muscular fatigue determination unit 406b calculates the level of muscular fatigue in the following manner if the first value is 188, the latest value is 230, and the muscular fatigue threshold is 30 in load group 4.

Level of muscular fatigue=100%×(230−188)/ 30=140%

Alternatively, the muscular fatigue determination unit 406b may calculate a difference between the difference described with reference to step S75 and the muscular fatigue threshold as the level of muscular fatigue. More specifically, the muscular fatigue determination unit 406b calculates the level of muscular fatigue in the following manner if the first value is 188, the latest value is 230, and the muscular fatigue threshold is 30 in load group 4.

Level of muscular fatigue=(230−188)−30=12

The muscular fatigue determination unit 406b may output a value calculated as the level of muscular fatigue to the output unit 407 to notify the user 100 of the level of muscular fatigue.

Figure 12A:
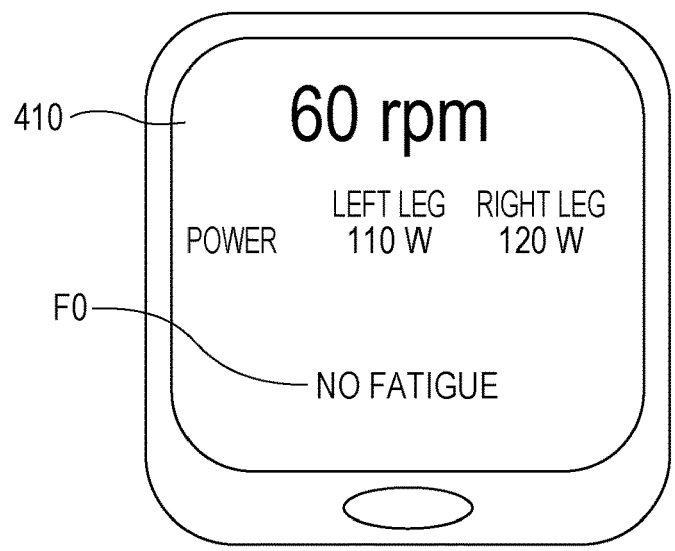
FIG. 12A is a diagram illustrating an example of a state of a user's muscle.
Figure 12B:
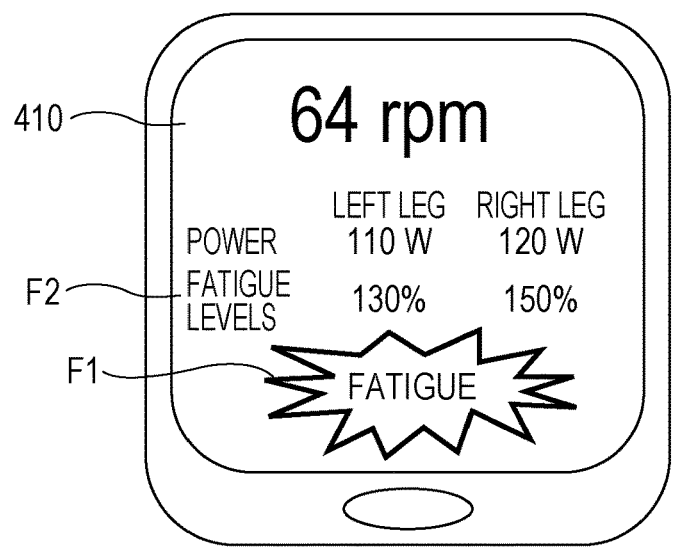
FIG. 12B is a diagram illustrating an example of the state of the user's muscle displayed.

Next, in step S77, information indicating presence or absence of muscular fatigue determined in step S75 and a result of the calculation of the level of muscular fatigue performed in step S76 are output to the output unit 407. The output unit 407 visually feeds information back to the user 100 by, for example, displaying these piece of information. As illustrated in FIGS. 12A and 12B, for example, a display unit 410 such as a liquid crystal display device, which is an example of the output unit 407, may display a rotation speed, power levels of left and right legs of the user 100, and a muscular fatigue state or the level of muscular fatigue to the user 100 along with an alarm icon or while issuing a warning tone. In FIG. 12A, muscular fatigue has not yet occurred, and the display unit 410 displays "no fatigue" F0. In FIG. 12B, muscular fatigue has occurred, and the display unit 410 displays "fatigue" F1 along with fatigue levels F2. The display unit 410 may display at least either presence or absence of muscular fatigue or the level(s) of muscular fatigue. Even if muscular fatigue has not occurred, the level(s) of muscular fatigue may be displayed. By displaying the level(s) of muscular fatigue, occurrence of muscular fatigue can be predicted.

Advantageous Effects Produced by Embodiment

With the above-described configuration, if the electromyograph 403a is attached to the user 100 and the user 100 pedals the bicycle 104 including the load sensor 401a and the rotation speed sensor 402a, muscular fatigue information including at least either information indicating presence or absence of muscular fatigue or the level of muscular fatigue can be generated in real-time. While the user 100 is rotating the crank 105 by stepping on the pedal 103 of the bicycle 104, the muscular fatigue information is generated on the basis of the myoelectric potential of the user 100, the load applied to the pedal 103, and the rotation speed (e.g., cadence, that is, the number of rotations of the crank 105 of the bicycle 104 per minute). Presence or absence of occurrence of muscular fatigue (a time at which muscular fatigue has occurred) or the level of muscular fatigue can thus be estimated. An invasive method such as measurement of blood lactic acid concentration need not be used, and since the storage unit 405 used for storing data is provided, preliminary calibration before pedaling is not necessary, thereby reducing a burden of the user 100.

Although the present disclosure has been described on the basis of an embodiment and modifications, the present disclosure is obviously not limited to the embodiment and the modifications. The present disclosure includes the following cases.

First information based on a first myoelectric potential difference of the user 100 who is rotating the crank 105 at a first rotation speed by applying first force to the pedal 103 of the bicycle 104 and second information based on a second myoelectric potential difference of the user 100 who is rotating the crank 105 at a second rotation speed by applying second force to the pedal 103 are obtained. This may be the following process.

The electromyograph 403a includes, for example, the electrodes 101b and 101c attached to the user 100 and detects a voltage between the electrodes 101b and 101c.

A plurality of first myoelectric potential differences are, for example, a total of 30 voltages, that is, myoelectric potential differences, between the electrodes 101b and 101c detected in 30 seconds at time intervals of 1 second. The first myoelectric potential difference is one of the 30 myoelectric potential differences. The first information may be an RMS of the 30 myoelectric potential differences. The first information may be an RMS of myoelectric potential differences such as "80" or "90" illustrated in FIG. 4B or 10.

A plurality of second myoelectric potential differences are, for example, a total of 30 voltages, that is, myoelectric potential differences, between the electrodes 101b and 101c detected in 30 seconds at time intervals of 1 second. The second myoelectric potential difference is one of the 30 myoelectric potential differences. The second information may be an RMS of myoelectric potential differences. The second information may be an RMS of myoelectric potential differences such as "115" or "110" illustrated in FIG. 4B or 10.

A first period, which is a period in which the plurality of first myoelectric potential differences are sampled, and a second period, which is a period in which the plurality of second myoelectric potential differences are sampled, may or may not overlap with each other insofar as the first period and the second period are not exactly the same. If myoelectric potential differences are sampled from a 1st second to a 600th second at time intervals of 1 second, for example, the first period may be from the 1st second to a 30th second and the second period may be from a 2nd second to a 31st second, or the first period may be from the 1st second to the 30th second and the second period may be from the 31st second to a 60th second. Third information based on the first force or first torque applied to the crank axle 110 of the crank 105 on the basis of the first force and fourth information based on the second force or second torque applied to the crank axle 110 of the crank 105 on the basis of the second force are obtained. This process may be the following process.

The load sensor 401a may be, for example, a force sensor attached to the pedal 103. The load sensor 401a detects force applied by the user 100 to the pedal 103.

A plurality of first force values are, for example, a total of 30 force values detected by the force sensor in 30 seconds at time intervals of 1 second. The first force is one of the 30 first force values. The third information may be an RMS or an average of the 30 force values. The third information corresponds to one of the load groups illustrated in FIG. 4B or 10 in accordance with a value thereof. The load groups illustrated in FIG. 4B or 10 may include load group 1 including loads equal to or higher than 0 N but lower than 1 N, load group 2 including loads equal to or higher than 1 N but lower than 2 N, load group 3 including loads equal to or higher than 2 N but lower than 3 N, and load group 4 including loads equal to or higher than 3 N.

A plurality of second force values are, for example, a total of 30 force values detected by the force sensor in 30 seconds at time intervals of 1 second. The second force is one of the 30 second force values. The fourth information may be an RMS or an average of the 30 force values. The fourth information corresponds to one of load groups 1 to 4 illustrated in FIG. 4B or 10 in accordance with a value thereof.

A third period, which is a period in which the plurality of first force values are sampled, may be the same as the first period, which is the period in which the plurality of first myoelectric potential differences are sampled. Timings at which the plurality of first force values are sampled may be synchronized with timings at which the plurality of first myoelectric potential differences are sampled.

A fourth period, which is a period in which the plurality of second force values are sampled, may be the same as the second period, which is the period in which the plurality of second myoelectric potential differences are sampled. Timings at which the plurality of second force values are sampled may be synchronized with timings at which the plurality of second myoelectric potential differences are sampled.

The load sensor 401a may be, for example, a torque sensor provided around the circumference of the crank axle 110, instead. The load sensor 401a detects torque applied to the crank axle 110, which is based on force applied by the user 100 to the pedal 103.

A plurality of first torque values are, for example, a total of 30 torque values detected by the torque sensor in 30 seconds at time intervals of 1 second. The first torque is one of the 30 first torque values. The third information may be an RMS or an average of the 30 torque values. The third information corresponds to one of load groups 1 to 4 illustrated in FIG. 4B or 10 in accordance with a value thereof. The load groups illustrated in FIG. 4B or 10 may include load group 1 including torque values equal to or larger than 0 N·m but smaller than 1 N·m, load group 2 including torque values equal to or larger than 1 N·m but smaller than 2 N·m, load group 3 including torque values equal to or larger than 2 N·m but smaller than 3 N·m, and load group 4 including torque values equal to or larger than 3 N·m.

A plurality of second torque values are, for example, a total of 30 torques detected by the torque sensor in 30 seconds at time intervals of 1 second. The second torque is one of the 30 second torque values. The fourth information may be an RMS or an average of the 30 torque values. The fourth information corresponds to one of load groups 1 to 4 illustrated in FIG. 4B or 10 in accordance with a value thereof.

The third period, which is the period in which the plurality of first torque values are sampled, may be the same as the first period, which is the period in which the plurality of first myoelectric potential differences are sampled. Timings at which the plurality of first torque values are sampled may be synchronized with the timings at which the plurality of first myoelectric potential differences are sampled.

The fourth period, which is the period in which the plurality of second torque values are sampled, may be the same as the second period, which is the period in which the plurality of second myoelectric potential differences are sampled. Timings at which the plurality of second torque values are sampled may be synchronized with the timings at which the plurality of second myoelectric potential differences are sampled.

Fifth information based on the first rotation speed and sixth information based on the second rotation speed are obtained. This process may be the following process.

The rotation speed sensor 402a is, for example, the rotation speed sensor 102 mounted on the pedal 103 and detects a speed at which the user 100 rotates the crank 105 connected to the pedal 103 by applying force to the pedal 103.

A plurality of first rotation speeds are, for example, a total of 30 rotation speeds detected by the rotation speed sensor 402a in 30 seconds at time intervals of 1 second. The first rotation speed is one of the 30 first rotation speeds. The fifth information may be an RMS or an average of the 30 rotation speeds. The fifth information is classified into one of the rotation speed groups illustrated in FIG. 4B or 10, namely "41→59" (rotation speeds from 41 to 59 rpm), "60→79" (rotation speeds from 60 to 79 rpm), and "80→100" (rotation speeds from 80 to 100 rpm), in accordance with a value thereof.

A plurality of second rotation speeds are, for example, a total of 30 rotation speeds detected by the rotation speed sensor 402a in 30 seconds at time intervals of 1 second. The second rotation speed is one of the 30 second rotation speeds. The sixth information may be an RMS or an average of the 30 rotation speeds. The sixth information is classified into one of the rotation speed groups illustrated in FIG. 4B or 10, namely "41→59" (rotation speeds from 41 to 59 rpm), "60→79" (rotation speeds from 60 to 79 rpm), and "80→100" (rotation speeds from 80 to 100 rpm), in accordance with a value thereof.

A fifth period, which is a period in which the plurality of first rotation speeds are sampled, may be the same as the first period, which is the period in which the plurality of first myoelectric potential differences are sampled. Timings at which the plurality of first rotation speeds are sampled may be synchronized with the timings at which the plurality of first myoelectric potential differences are sampled.

A sixth period, which is a period in which the plurality of second rotation speeds are sampled, may be the same as the second period, which is the period in which the plurality of second myoelectric potential differences are sampled. Timings at which the plurality of second rotation speeds are sampled may be synchronized with the timings at which the plurality of second myoelectric potential differences are sampled.

If the third information and the fourth information belong to the same category among a plurality of categories, seventh information and eighth information are compared with each other. Each of the plurality of categories is defined on the basis of a predetermined force or torque range. The first information is corrected to the seventh information on the basis of the third information and the fifth information. The larger the fifth information, the smaller the seventh information. The second information is corrected to the eighth information on the basis of the fourth information and the sixth information. The larger the sixth information, the smaller the eighth information. This process may be the following process.

Correspondences between the load, the rotation speed, and the myoelectric potential (before correction) and the above-described pieces of information in FIG. 9 and the related description are: (load, rotation speed, myoelectric potential (before correction))=(third information, fifth information, first information); and (load, rotation speed, myoelectric potential (before correction))=(fourth information, sixth information, second information).

In the classification of a load in step S71, the third information and the fourth information, which are information relating to force or torque, are classified into one of load groups 1 to 4 in accordance with the values thereof. The plurality of categories are, for example, load groups 1 to 4.

The first information and the second information have not been subjected to the correction process in step S72. Information obtained by performing the correction process in step S72 on the first information is the seventh information, and information obtained by performing the correction process in step S72 on the second information is the eighth information. The correction process is performed while referring to a table illustrated in FIG. 11A. Classification into one of the load groups illustrated in FIG. 11A may be performed, for example, using an RMS or an average of a total of 30 force values detected by the force sensor in 30 seconds at time intervals of 1 second. The classification into one of the load groups illustrated in FIG. 11A may be performed, for example, using an RMS or an average of a total of 30 torque values detected by the torque sensor in 30 seconds at time intervals of 1 second. Classification into one of the rotation speed groups illustrated in FIG. 11A may be performed, for example, using an RMS or an average of a total of 30 rotation speeds detected by the rotation speed sensor 402a in 30 seconds at time intervals of 1 second. An RMS or an average of a total of 30 myoelectric potential differences detected by the electromyograph 403a in 30 seconds at time intervals of 1 second may be corrected using the table illustrated in FIG. 11A.

It is assumed, for example, that myoelectric potential differences are sampled for 30 seconds at time intervals of 1 second, and an RMS or an average of these 30 myoelectric potential differences, which is the first information, is obtained. Force values may be sampled for 30 seconds at time intervals of 1 second in synchronization with the sampling of the myoelectric potential differences, and an RMS or an average of these 30 force values, which is the third information, may be obtained. Alternatively, torque values may be sampled for 30 seconds at time intervals of 1 second in synchronization with the sampling of the myoelectric potential differences, and an RMS or an average of these 30 torque values, which is the third information, may be obtained. Rotation speeds are sampled for 30 seconds at time intervals of 1 second in synchronization with the sampling of the myoelectric potential differences, and an RMS or an average of these 30 rotation speeds, which is the fifth information, is obtained. The first information (e.g., the RMS of myoelectric potential differences) is then corrected while referring to the table of FIG. 11A. If the third information (e.g., the RMS of the force values or the RMSs of torque values) belongs to load group 1 and the fifth information (e.g., the RMS of rotation speeds) belongs to the rotation speed group "80→100", for example, the first information is multiplied by 0.8. On the other hand, if the third information belongs to load group 1 and the fifth information belongs to the rotation speed group "40→59", for example, the first information is multiplied by 1.1. That is, correction is performed such that the first information becomes smaller as the fifth information becomes larger. The first information corrected as illustrated in FIG. 11B is recorded in the database as the seventh information.

It is assumed, for example, that myoelectric potential differences are sampled for 30 seconds at time intervals of 1 second, and an RMS or an average of these 30 myoelectric potential differences, which is the second information, is obtained. Force values may be sampled for 30 seconds at time intervals of 1 second in synchronization with the sampling of the myoelectric potential differences, and an RMS or an average of these 30 force values, which is the fourth information, may be obtained. Alternatively, torque values may be sampled for 30 seconds at time intervals of 1 second in synchronization with the sampling of the myoelectric potential differences, and an RMS or an average of these 30 torque values, which is the fourth information, may be obtained. Rotation speeds are sampled for 30 seconds at time intervals of 1 second in synchronization with the sampling of the myoelectric potential differences, and an RMS or an average of these 30 rotation speeds, which is the sixth information, is obtained. The second information (e.g., the RMS of myoelectric potential differences) is then corrected while referring to the table illustrated in FIG. 11A. If the fourth information (e.g., the RMS of force values or the RMSs of the torque values) belongs to load group 1 and the sixth information (e.g., the RMS of rotation speeds) belongs to the rotation speed group "80→100", for example, the second information is multiplied by 0.8. On the other hand, if the fourth information belongs to load group 1 and the sixth information belongs to the rotation speed group "40→59", for example, the second information is multiplied by 1.1. That is, correction is performed such that the second information becomes smaller as the fifth information becomes larger.

As illustrated in FIG. 11B, the corrected second information is recorded in the database as the eighth information.

In step S75, a change in the RMS of myoelectric potential differences in the same load group after the correction is obtained. That is, the seventh information and the eighth information are compared with each other. In the comparison, for example, changes in the seventh information and the eighth information may be obtained.

Part or the entirety of each muscular fatigue determination apparatus is specifically a computer system including a microprocessor, a read-only memory (ROM), a random-access memory (RAM), a hard disk unit, a display unit, a keyboard, and a mouse. The RAM or the hard disk unit is used for storing a computer program. The microprocessor operates in accordance with the computer program, and the components of each muscular fatigue determination apparatus achieve functions thereof. The computer program includes a plurality of command codes indicating instructions to the computer system to achieve certain functions.

The information obtaining unit 400, for example, can also be referred to as an information obtaining circuit that obtains information. The muscular fatigue information generation unit 399 can also be referred to as a muscular fatigue information generation circuit that determines muscular fatigue in a user on the basis of information obtained by the information obtaining circuit. A general-purpose processor such as a central processing unit (CPU), however, can also operate as the information obtaining unit 400 and the muscular fatigue information generation unit 399. The information obtaining unit 400 and the muscular fatigue information generation unit 399 may therefore be a CPU of a personal computer (PC), a smartphone, or a tablet.

The components can be realized by, for example, reading a software program recorded on a recording medium such as a hard disk or a semiconductor memory using a program execution unit of a CPU or the like. Software for realizing part or all of the components of the muscular fatigue determination apparatus according to the embodiment or one of the modifications is the following program. That is, the program is a muscular fatigue determination program for causing a computer to function as: an information obtainer that obtains a load applied to a pedal of a bicycle, rotation speed of a crank of the bicycle, and a myoelectric potential of a user corresponding to the load and the rotation speed, and a muscular fatigue information generator that generates muscular fatigue information regarding the user on the basis of whether a difference between a plurality of myoelectric potentials of the user corresponding to loads and rotation speeds within a certain range is larger than a first threshold.

The program may be downloaded from a server or the like and executed, or may be read from a certain recording medium (e.g., an optical disc such as a CD-ROM, a magnetic disk, or a semiconductor memory) and executed.

A computer or a plurality of computers may execute the program. That is, centralized processing or distributed processing may be performed.

By appropriately combining the above embodiment and modifications, corresponding advantageous effects can be produced. In addition, embodiments may be combined with each other, examples may be combined with each other, and an embodiment and an example may be combined with each other. Characteristics described in different embodiments or examples may be combined with each other.

According to the muscular fatigue determination apparatus and the method for determining muscular fatigue, muscular fatigue information can be generated in real-time while a user is pedaling a bicycle. The muscular fatigue determination apparatus and the method for determining muscular fatigue are effective when a bicycle or a cycle trainer is used in a sport field or a rehabilitation field. That is, the user can measure a myoelectric potential using an electromyograph attached thereto and estimate muscular fatigue in real-time. The user can therefore visually check a state of the muscle thereof in training for competition or general exercise by simply using an output of an output unit. This allows the user to improve a technique for adjusting a pedaling pace or moving muscle through an exercise menu. The muscular fatigue determination apparatus and the method for determining muscular fatigue can be introduced to the rehabilitation field as well as the sport field. If the electromyograph is reduced in size, the user can easily use the muscular fatigue determination apparatus and the method for determining muscular fatigue in a rehabilitation facility or for a rehabilitation apparatus at home.

What is claimed is:

1. A muscular fatigue determination apparatus comprising:
    a load detector that detects loads applied to a pedal of a bicycle;
    a rotation speed detector that detects rotation speeds of a crank of the bicycle;
    a myoelectric potential detector that detects myoelectric potentials of a user;
    an information obtainer that obtains the loads, the rotation speeds, and the myoelectric potentials, the myoelectric potentials and the loads being in a one-to-one relationship, the myoelectric potentials and the rotation speeds being in a one-to-one relationship; and
    a muscular fatigue information generator that generates muscular fatigue information regarding the user on the basis of whether a difference between the myoelectric potentials of the user is larger than a first threshold, each of the myoelectric potentials being associated to a load range that is one of load ranges and to a rotation speed range that is one of rotation speed ranges, each of the loads belonging to one of the load ranges and each of the rotation speed ranges belonging to one of the rotation speed ranges,
    wherein the information obtainer further includes a load classifier that classifies each of the loads obtained by the information obtainer into one of a plurality of load groups on the basis of a value of the load, and
    wherein the muscular fatigue information generator compares the myoelectric potentials in the same load group with each other for each of the plurality of load groups into which loads have been classified by the load classifier and generates the muscular fatigue information regarding the user.

2. The muscular fatigue determination apparatus according to claim 1,
    wherein, if the difference between the myoelectric potentials of the user is larger than the first threshold, the muscular fatigue information generator generates muscular fatigue information regarding the user indicating that muscular fatigue has occurred.

3. The muscular fatigue determination apparatus according to claim 1,
    wherein the information obtainer obtains the loads, the rotation speeds, and the myoelectric potentials of the user while associating the loads, the rotation speeds, and the myoelectric potentials of the user with a point of time, and wherein the muscular fatigue information generator generates the muscular fatigue information regarding the user on the basis of whether a difference between the myoelectric potentials of the user each corresponding to the load range that is one of the load ranges and to the rotation speed range that is one of the rotation speed ranges, and each associated with different points of time is larger than the first threshold.

4. The muscular fatigue determination apparatus according to claim 1, further comprising:

an outputter that outputs the muscular fatigue information generated by the muscular fatigue information generator.

5. The muscular fatigue determination apparatus according to claim 1, wherein the information obtainer further includes a myoelectric potential corrector that corrects a myoelectric potential corresponding to one of the load groups into which the load has been classified by the load classifier, the myoelectric potentials including the myoelectric potential, the correction being made based on the rotation speed corresponding to the myoelectric potential, and wherein, when comparing the myoelectric potentials in the same load group with each other for each of the plurality of load groups into which the loads have been classified by the load classifier, the muscular fatigue information generator compares the myoelectric potentials with each other using the myoelectric potential corrected by the myoelectric potential corrector and generates the muscular fatigue information regarding the user.

6. The muscular fatigue determination apparatus according to claim 1, wherein the muscular fatigue information generator includes a myoelectric potential comparer that obtains a difference between a first myoelectric potential and a latest myoelectric potential in the same load group among the plurality of load groups into which the loads have been classified by the load classifier, the myoelectric potentials of the user include the first myoelectric potential and the latest myoelectric potential, and a muscular fatigue determiner that, if the difference between the myoelectric potentials obtained by the myoelectric potential comparer is larger than the first threshold, determines that muscular fatigue has occurred.

7. The muscular fatigue determination apparatus according to claim 6, wherein, when comparing the myoelectric potentials in the same load group with each other, the muscular fatigue information generator uses a load group for largest loads among the plurality of load groups into which the loads have been classified by the load classifier.

8. The muscular fatigue determination apparatus according to claim 6, wherein, if generating muscular fatigue information regarding the user indicating that muscular fatigue has occurred, the muscular fatigue information generator calculates a difference between the myoelectric potentials in the same load group and the first threshold as a level of muscular fatigue and outputs the level of muscular fatigue.

9. A method for determining muscular fatigue, the method comprising:

obtaining, with an information obtainer, loads, rotation speeds, and myoelectric potentials of a user, using a load detector that detects the loads applied to a pedal of a bicycle, a rotation speed detector that detects the rotation speeds of a crank of the bicycle, and a myoelectric potential detector that detects the myoelectric potentials, the myoelectric potentials and the loads being in a one-to-one relationship, the myoelectric potentials and the rotation speeds being in a one-to-one relationship; and generating, with a muscular fatigue information generator, muscular fatigue information regarding the user on the basis of whether a difference between the myoelectric potentials of the user is larger than a first threshold, each of the myoelectric potentials of the user being associated to a load range that is one of load ranges and to a rotation speed range that is one of rotation speed ranges, each of the loads belonging to one of the load ranges and each of the rotation speed ranges belonging to one of the rotation speed ranges, wherein said obtaining further comprises classifying each of the loads into one of a plurality of load groups on the basis of a value of the load, and wherein said generating comprises comparing the myoelectric potentials in the same load group with each other for each of the plurality of load groups into which loads have been classified and generating the muscular fatigue information regarding the user.

10. A recording medium storing a control program for causing a device including a processor to execute a process, the recording medium being a nonvolatile computer-readable recording medium, the process comprising:

obtaining loads applied to a pedal of a bicycle, rotation speeds of a crank of the bicycle, and myoelectric potentials of a user, the myoelectric potentials and the loads being in a one-to-one relationship, the myoelectric potentials and the rotation speeds being in a one-to-one relationship; and generating muscular fatigue information regarding the user on the basis of whether a difference between the myoelectric potentials of the user is larger than a first threshold, each of the myoelectric potentials of the user being associated to a load range that is one of load ranges and to a rotation speed range that is one of rotation speed ranges, each of the loads belonging to one of the load ranges and each of the rotation speed ranges belonging to one of the rotation speed ranges, wherein said obtaining further comprises classifying each of the loads into one of a plurality of load groups on the basis of a value of the load, and wherein said generating comprises comparing the myoelectric potentials in the same load group with each other for each of the plurality of load groups into which loads have been classified and generating the muscular fatigue information regarding the user.

* * * * *